United States Patent
Berry et al.

(10) Patent No.: US 7,572,609 B2
(45) Date of Patent: Aug. 11, 2009

(54) PRODUCTION OF ISOPRENOIDS

(75) Inventors: Alan Berry, Manlius, NY (US);
Christian Manhart, Basel (CH); Petra Simic, Basel (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/632,280

(22) PCT Filed: Aug. 11, 2005

(86) PCT No.: PCT/EP2005/008702

§ 371 (c)(1),
(2), (4) Date: Jan. 12, 2007

(87) PCT Pub. No.: WO2006/018211

PCT Pub. Date: Feb. 23, 2006

(65) Prior Publication Data
US 2007/0202579 A1    Aug. 30, 2007

(30) Foreign Application Priority Data
Aug. 19, 2004  (EP)  ................................. 04019646

(51) Int. Cl.
*C12P 7/66*   (2006.01)
*C12N 15/74*  (2006.01)
*C07H 21/04*  (2006.01)

(52) U.S. Cl. .................. 435/133; 435/252.3; 536/23.2; 536/23.1

(58) Field of Classification Search ........................ None
See application file for complete search history.

(56) References Cited

FOREIGN PATENT DOCUMENTS

| EP | 0 955 363 A2 | 11/1999 |
|---|---|---|
| WO | 99/06586 | 2/1999 |
| WO | 02/099095 A2 | 12/2002 |
| WO | WO2005000565 | * 1/2005 |

OTHER PUBLICATIONS

Chica et al. (Curr Opin Biotechnol. Aug. 2005; 16(4):378-84.*
International Search Report of PCT/EP2005/008702, mailed Oct. 26, 2005.
Wilding et al. "Identification, Evolution, and Essentiality of the Mevalonate Pathway for Isopentenyl Diphosphate Biosynthesis in Gram-Positive Cocci" Journal of Bacteriology, vol. 182, No. 15, pp. 4319-4327, Aug. 2000.
Humbelin et al. "Genetics of Isoprenoid Biosynthesis in *Paracoccus zeaxanthinifaciens*" Gene, vol. 297, No. 1-2, pp. 129-139, Sep. 4, 2002.

* cited by examiner

*Primary Examiner*—Nashaat T Nashed
*Assistant Examiner*—Md. Younus Meah
(74) *Attorney, Agent, or Firm*—Nixon & Vanderhye P.C.

(57) ABSTRACT

The present invention relates to a process for the production of isoprenoids Coenzyme Q-10 by microorganisms. More particularly, the present invention relates to a process for increased production of Coenzyme Q-10 by microorganisms of the genus *Rhodobacter*, preferably of the species *R. sphaeroides* which have been transformed with one or more gene(s) of the mevalonate (mev) operon from a different microorganism, preferably of the genus *Paracoccus*, more preferably of the species *P. zeaxanthinifaciens*, whereby the mev operon is mutated leading to an increased coenzyme Q-10 production. Sequences carrying such a mutation as well as a microorganism carrying such a mutated mev operon are also included.

23 Claims, 1 Drawing Sheet

PRODUCTION OF ISOPRENOIDS

Figure 1:
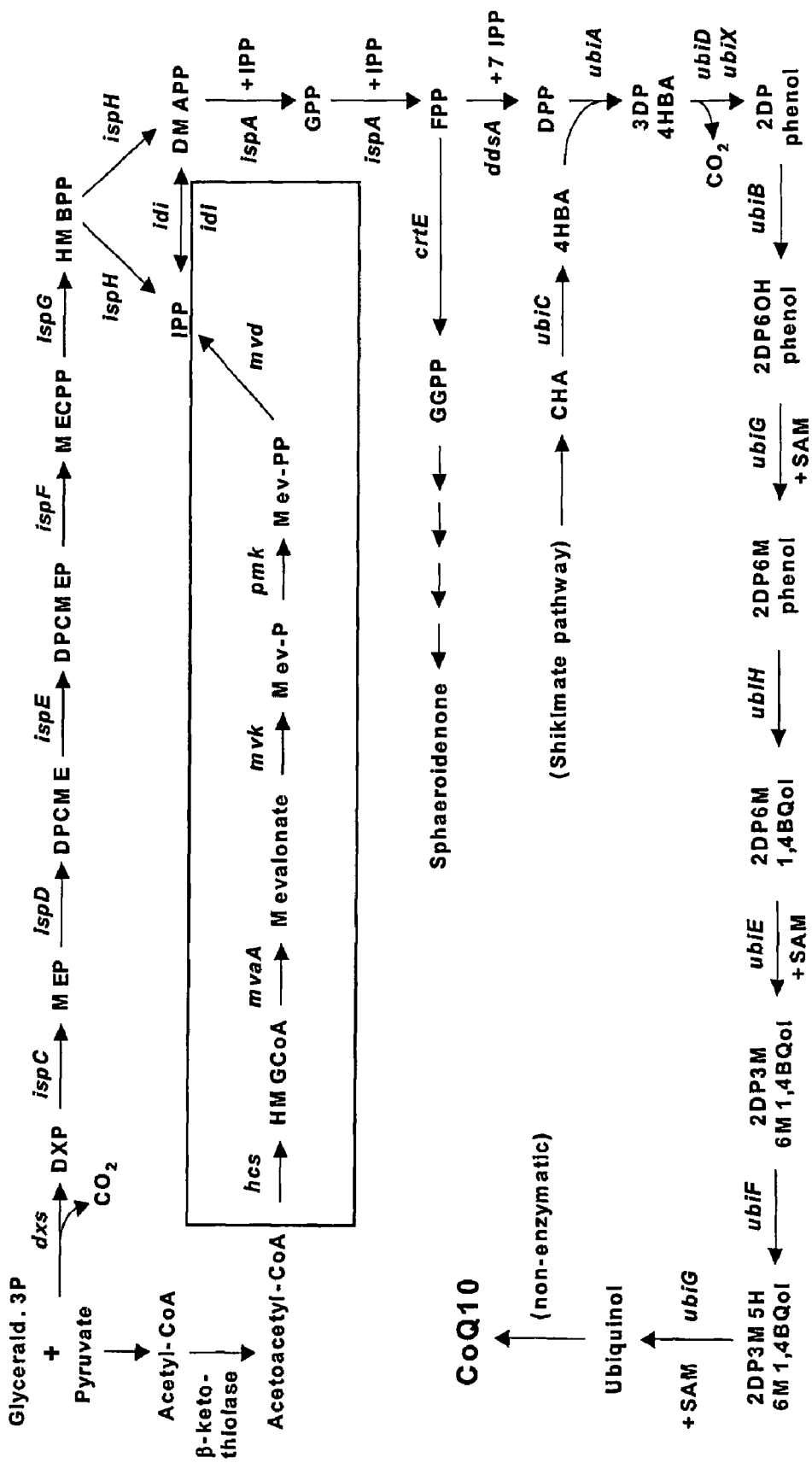

This application is the U.S. national phase of International Patent Application No. PCT/EP2005/008702, filed 11 Aug. 2005, which designated the U.S. and claims priority of EP 04019646.1, filed 19 Aug. 2004; the entire contents of each of which are hereby incorporated by reference.

The present invention relates to a process for the production of isoprenoids, in particular Coenzyme Q-10 by microorganisms. More particularly, the present invention relates to a process for increased production of Coenzyme Q-10 by microorganisms of the genus *Rhodobacter*, preferably of the species *R. sphaeroides* which have been transformed with one or more gene(s) of the mevalonate (mev) operon from a different microorganism, preferably of the genus *Paracoccus*, more preferably of the species *P. zeaxanthinifaciens*, whereby the mev operon is mutated leading to an increased coenzyme Q-10 production. Sequences carrying such a mutation as well as a microorganism carrying such a mutated mev operon are also included.

Coenzyme Q-10 (2,3-dimethoxy-dimethyl-6-decaprenyl-1,4-benzoquinone), also known as ubiquinone-10, is a lipid-soluble benzoquinone having an isoprenoid side chain comprised of ten C-5 isoprenoid units. Coenzyme Q-10 (hereafter abbreviated as CoQ10) is found in microorganisms and plants, as well as in animals. It is the most prevalent form of ubiquinone in humans and most mammals. There is established and growing evidence that CoQ10 is an important factor in the health status of humans and their protection from diseases. The medical and health beneficial effects of CoQ10 have been associated with its two main physiological functions, namely to function as an essential cofactor of the mitochondrial electron transport chain (which is coupled to the synthesis of adenosine triphosphate) and to act as a lipid soluble antioxidant.

The health benefits of CoQ10 have led to increased commercial importance of this compound. CoQ10 can be produced by chemical synthesis or by fermentation using microorganisms. These microorganisms may be natural CoQ10 producers that have been improved for CoQ10 production by genetic engineering, or they may not naturally produce CoQ10 but have been manipulated by genetic engineering to be able to synthesize it.

In bacteria, the quinoid ring of ubiquinones is derived from chorismate, a central intermediate in the biosynthesis of aromatic compounds, while the isoprenoid tail of ubiquinones is derived from the C-5 compound isopentenyl pyrophosphate (IPP). The length of the isoprenoid tail added to the quinoid ring depends of the particular prenyltransferase enzyme that exists in the bacterium. For example, in *Escherichia coli*, octaprenyl pyrophosphate synthase catalyzes the formation of octaprenyl pyrophosphate (C-40) from farnesyl pyrophosphate (FPP, C-15) and five IPP units. Addition of this molecule to the quinoid ring results in formation of ubiquinone-8. In *Paracoccus* and *Rhodobacter* species, decaprenyl pyrophosphate (DPP) synthase catalyzes the formation of DPP (C-50) from FPP (C-15) and seven IPP units. Addition of DPP to the quinoid ring then results in formation of ubiquinone-10 (CoQ10).

In nature, two different pathways are known for the biosynthesis of IPP (FIG. 1). The mevalonate pathway, as its name implies, utilizes mevalonate as a central intermediate and has been well studied in eukaryotes. The mevalonate pathway was thought for many years to be the universal pathway of IPP synthesis in nature. However, in the last decade a second pathway of IPP biosynthesis, called non-mevalonate pathway or the MEP pathway (as it has 2C-methyl-D-erythritol 4-phosphate as an intermediate) was discovered. The MEP pathway has so far been shown to exist in many eubacteria and in the plastid compartment of higher plants.

Based on the presence in *R. sphaeroides* of the yaeM gene (now called ispC) coding for 1-deoxy-D-xylulose 5-phosphate reductoisomerase and on inspection of the nearly completed genome sequence of *R. sphaeroides*, it appears that this bacterium uses exclusively the MEP pathway for biosynthesis of IPP. Additional evidence supporting the exclusive use of the MEP pathway in *R. sphaeroides* is the finding that a closely related species, *Rhodobacter capsulatus*, uses only the MEP pathway for isoprenoid biosynthesis.

WO 02/26933 A1 discloses methods for increasing the production of CoQ10 in *Rhodobacter sphaeroides* by overexpressing a few native and/or heterologous genes coding for some of the enzymes of the MEP pathway. However, the overexpression of these genes resulted in only very modest improvement in CoQ10 production.

As mentioned above, some bacteria use only the mevalonate pathway for biosynthesis of IPP. *Paracoccus zeaxanthinifaciens* is an example of such a bacterium. In *P. zeaxanthinifaciens*, the genes coding for the five enzymes of the mevalonate pathway, plus the gene coding for IPP isomerase (see FIG. 1), are clustered together in a single transcriptional unit on the chromosome, ie., an operon called hereinafter the mevalonate (mev) operon (Hümbelin et al., Gene 297, 129-139, 2002).

It has now been found that the production of isoprenoids, in particular CoQ10 can be significantly increased by the introduction of a mutated mev operon into a microorganism which is naturally deficient of one or more gene(s) of the mev operon, i.e. naturally using the non-mevalonate pathway for the production of isoprenoids, wherein either the complete mev operon or one or more gene(s) of said mev operon comprising one or more mutation(s) may be introduced. The one or more mutation may be for instance in one or all of the following genes: mvaA encoding hydroxymethylglutaryl-CoA reductase, idi encoding isopentenyl diphosphate isomerase, hcs encoding hydroxymethylglutaryl-CoA synthase, mvk encoding mevalonate kinase, pmk encoding phosphomevalonate kinase, and mvd encoding diphosphomevalonate decarboxylase.

Thus, the present invention provides a polynucleotide sequence comprising one or more gene(s) encoding a protein having hydroxymethylglutaryl-CoA reductase activity, isopentenyl diphosphate isomerase activity, hydroxymethylglutaryl-CoA synthase activity, mevalonate kinase activity, phosphomevalonate kinase activity, and/or diphosphomevalonate decarboxylase activity, wherein said polynucleotide sequence carries one or more mutation(s) leading to an improved production of isoprenoids when present in a microorganism. The improvement in isoprenoid production may be measured for instance by a comparison of the production in a wild-type microorganism not carrying said polynucleotide sequences, i.e. not using the mev pathway, with the microorganism carrying a polynucleotide sequence as of the present invention.

In one embodiment, the present invention is directed to a polynucleotide sequence which is obtainable from SEQ ID NO: 1 or 2, i.e. comprising genes of the wild-type mev operon, or a fragment thereof, wherein the fragment has the activity of at least one of the genes of the mev operon, e.g., mvaA encoding hydroxymethylglutaryl-CoA reductase, idi encoding isopentenyl diphosphate isomerase, hcs encoding hydroxymethylglutaryl-CoA synthase, mvk encoding mevalonate kinase, pmk encoding phosphomevalonate kinase, and mvd encoding diphosphomevalonate decarboxylase. Preferably, the mutated polynucleotide sequence is represented by SEQ ID NO:3 or a fragment thereof, leading to an increase in e.g. CoQ10 production when present in a microorganism.

In one aspect, the present invention relates to a DNA sequence comprising a mev operon carrying a mutation, said DNA sequence being represented by SEQ ID NO:3.

The term "improved isoprenoid production", in particular improved CoQ10 production, as used herein means for instance an increase of at least about 10% obtained by a microorganism carrying a polynucleotide comprising one or more mutation(s) as described above when compared to the respective microorganism carrying the respective wild-type polynucleotide. The production of the isoprenoids is measured by standard methods, e.g. HPLC (see Example 2) and may be expressed in mg/l or as mg/l/$OD_{600}$ (see Example 5).

The complete mev operon or one or more gene(s) thereof carrying one or more mutation(s) may be for instance either totally synthesized or partially isolated and synthesized. An isolated Rev operon or one or more gene(s) thereof may originate from any microorganism using the mevalonate pathway, i.e. wherein one or more gene(s) included within said operon are naturally occurring. Preferably, the microorganism belongs to the genus *Paracoccus*, more preferably from *Paracoccus zeaxanthinifaciens*, such as, e.g. *Paracoccus* sp. R114 or *P. zeaxanthinifaciens* ATCC 21588. Allelic variations and mutants of the DNA sequence of the operon which are fully functional are also comprised by the above term. The complete mev operon of *P. zeaxanthinifaciens* ATCC 21588 is shown in SEQ ID NO:1, the complete mev operon of *Paracoccus* sp. R114 is shown in SEQ ID NO:2 (see also SEQ ID NO:42 of WO 02/099095).

Strain *Paracoccus* sp. R114 is a derivative of *P. zeaxanthinifaciens* ATCC 21588 and has been deposited under the terms of the Budapest Treaty with ATCC under the Patent Deposit Designation PTA-3335 on Apr. 24, 2001. With respect to *Paracoccus* species and strains which may be used for the present invention and the taxonomic reclassification of *Flavobacterium* sp. as *Paracoccus* reference is made to WO 02/099095, pages 47ff. Examples of such species which may be used are *P. marcusii, P. carotinifaciens, P. solventivorans, P. zeaxanthinifaciens* or *Paracoccus* sp. R114.

The mev operon of the present invention carries one or more mutation(s) which may be located at any position within the operon, leading to an alteration in the activity of one or more gene(s) within said operon, resulting in an improved production of isoprenoids within a microorganism carrying such polynucleotide.

In one embodiment, the mev operon carries at least one mutation, which is preferably located in the hcs gene of the mev operon, for instance in the hcs gene of the mev operon of *Paracoccus zeaxanthinifaciens*, e.g. in the hcs gene of the mev operon of *Paracoccus* sp. R114 or *P. zeaxanthinifaciens* ATCC 21588. More preferably, the mutated mev operon as used in the present invention is represented by SEQ ID NO:3. The sequences of the wild-type hcs gene and the respective protein of *Paracoccus* sp. R114 are shown in SEQ ID NO:4 and 5, respectively.

In one embodiment, the present invention is directed to a polynucleotide comprising one or more mutation(s) in the hcs gene, preferably a polynucleotide shown in SEQ ID NO:6 encoding a protein having hydroxymethylglutaryl-CoA synthase shown in SEQ ID NO:7, wherein a glutamine present on position 90 in SEQ ID NO:5 is replaced by a lysine.

Thus, it is an object of the present invention to provide a polynucleotide sequence as described before comprising one or more gene(s) of a mev operon, said polynucleotide being selected from the group consisting of:

(a) polynucleotides encoding a polypeptide comprising the amino acid sequence according the SEQ ID NO:7,
(b) polynucleotides comprising the nucleotide sequence according to SEQ ID NO:6,
(c) polynucleotides comprising a nucleotide sequence encoding a fragment or derivative of a polypeptide encoded by a polynucleotide of (a) or (b) wherein in said derivative one or more amino acid residues are conservatively substituted compared to said polypeptide, and said fragment or derivative has the activity of hydroxymethylglutaryl-CoA synthase (Hcs);
(d) polynucleotides the complementary strand of which hybridizes under stringent conditions to a polypeptide as defined in any one of (a) to (c) and which encodes a Hcs protein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of proteins may exist within a population.

The invention also relates to an isolated polynucleotide hybridisable under stringent conditions, preferably under highly stringent conditions, to a polynucleotide as of the present invention, such as for instance a polynucleotide shown in SEQ ID NO:6.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g. practically any double-stranded cDNA clone).

The present invention can be used for the production of isoprenoids, in particular ubiquinones, preferably CoQ10. Preferably, the polynucleotides comprising one or more mutation(s), i.e. either the complete mev operon or only fragments thereof, are introduced into a suitable microorganism which is originally deficient of one or more gene(s) of the mev operon, i.e. naturally using only the MEP pathway for the production of isoprenoids.

The mutated mev operon or one or more gene(s) thereof as described above may be for instance introduced into a microorganism of the genus *Rhodobacter*.

In particular, the present invention is directed to a process for the production of isoprenoids, in particular ubiquinones, preferably CoQ10, comprising (1) introducing a polynucleotide as of the present invention into a microorganism which is originally deficient of said polynucleotides, and (2) cultivating the microorganism of step (1) under conditions that allow the production of the isoprenoid. Preferably, the mutated mev operon or fragments thereof of a microorganism belonging to the genus *Paracoccus* is introduced into a microorganism belonging to the genus *Rhodobacter*. More preferably, a polynucleotide comprising one or more mutation(s) in the gene encoding hydroxymethylglutaryl-CoA synthase is introduced into said microorganism, and most preferred is the introduction of a polynucleotide sequence represented by SEQ ID NO:3.

Any microorganism which is originally deficient of one or more gene(s) of the mev operon, i.e. using the MEP pathway for the production of isoprenoids, may be used for the purpose of the present invention. In particular microorganisms of the genus *Rhodobacter* may be used for the introduction of a mutated polynucleotide as of the present invention, such as for instance *R. sphaeroides*, *R. adriaticus*, *R. capsulatus*, *R. sulfidophilus*, or *R. veldkampii*. A preferred strain is *R sphaeroides*, even more preferred is *R. sphaeroides* ATCC 35053.

It is understood that the microorganisms as named herein also include synonyms or basonyms of such species having the same physico-chemical properties, as defined by the International Code of Nomenclature of Prokaryotes.

The present invention further provides recombinant microorganisms which having introduced a polynucleotide described above, i.e. comprising one of more gene(s) of a mev operon carrying one or more mutation(s), wherein the respective wild-type microorganism is originally deficient of one or more gene(s) of the mev operon, i.e. using the MEP pathway for production of isoprenoids, leading to an improved production of isoprenoids, particularly ubiquinones, preferably CoQ10, compared to the respective wild-type microorganism.

Besides the mutation within the one or more gene(s) of the mev operon as described above, the recombinant microorganism may contain further modifications/alterations as long as they lead to an improvement in the production of isoprenoids within said microorganism.

In one embodiment, such further modification is the introduction of a DNA sequence encoding a protein having decaprenyl diphosphate synthase activity into said recombinant microorganism, preferably obtainable from a microorganism of the genus *Paracoccus*, e.g., *P. zeaxanthinifaciens*, in particular *P. zeaxanthinifaciens* ATCC 21588. Most preferred is a polynucleotide sequence as of SEQ ID NO:8 or a polynucleotide encoding a protein as of SEQ ID NO:9.

Thus, the present invention is directed to a process for the production of isoprenoids, preferably CoQ10 as above wherein a DNA sequence encoding a protein having decaprenyl diphosphate synthase activity is further introduced into a microorganism which is naturally using the MEP pathway and has one or more gene(s) of the mev operon comprising one or more mutation(s) introduced as described above, e.g. a microorganism of the genus *Rhodobacter*.

Thus, it is an aspect of this invention to provide a process for the production of CoQ10 comprising (1) introducing both a mevalonate (mev) operon and a DNA sequence encoding a protein having decaprenyl diphosphate synthase activity of a microorganism belonging to the genus *Paracoccus* into a microorganism belonging to the genus *Rhodobacter*, wherein said mev operon carries one or more mutation(s) and (2) cultivating the modified *Rhodobacter* strain.

The term "introducing into" is used in the present specification and claims in connection with the transformation of a microorganism or host organism, e.g. of the genus *Rhodobacter*, to comprise any method well-known to a person skilled in the art which may be used to efficiently bring genetic material, in particular the mutated mevalonate operon or one or more gene(s) thereof, into the host organism, i.e. in a way that it is expressed by the organism. Introduction may be effected, e.g. by vectors, preferably expression plasmids or by integration into the host's genome in accordance with standard methods. A preferred method is the introduction of genes via plasmids, such as for instance genes which are cloned in the expression plasmid pBBR-K-PcrtE (the construction of this plasmid has been described in detail in Example 6, page 91, lines 12-27 of WO 02/099095) under the control of the PcrtE promoter. A preferred method for introducing the DNA such as for instance the expression plasmid into a microorganisms of the genus *Rhodobacter* is the conjugational transfer of plasmids, such as for instance conjugational transfer of a plasmid from *E. coli* S17-1 to a *Rhodobacter* strain (Nishimura et al., Nucl. Acids Res. 18, 6169, 1990; Simon et al., Bio/Technology 1983, 784-91).

The mutation(s) of the mev operon or of one or more gene(s) thereof may be generated by for instance PCR site directed mutagenesis using a method with which a person skilled in the art is familiar and which needs no specific explanation. Further mutagenesis methods, which may be also used for the purpose of the present invention and which are known to the skilled person include for instance UV irradiation, transposition or chemical mutagenesis. The screening method for identification of mutants showing increased isoprenoid, e.g. CoQ10, productivity maybe for instance selected from direct measurement of isoprenoids, e.g. CoQ10, by UV light, HPLC, NMR or thin layer chromatography. Production of isoprenoids, e.g. CoQ10, may be also measured indirectly via measuring an increase in carotenoid color intensity, which a person skilled in the art is familiar with.

The host transformed with the mutated mev operon or one or more gene(s) thereof as of the present invention may be cultivated in accordance with known methods, viz. in a medium containing for instance carbon and nitrogen sources, inorganic salts, etc., which may be assimilated by the host and under temperature, pH and aeration conditions suitable for efficient growing and expression of the desired product, in particular CoQ10.

Isolation from the fermentation broth and/or the transformant, i.e. the microorganism in which the mutated mevalonate operon of a microorganism belonging e.g. to the genus *Paracoccus* has been introduced, and, optionally, purification and further processing of the obtained isoprenoid, in particular CoQ10, including for instance formulations of such produced CoQ10 for human or animal usage may be effected in accordance with methods well-known in the art. For use in animal health and nutrition, however, no specific purification may be necessary. In this case the produced isoprenoids like CoQ10 together with the biomass and/or other components of the fermentation broth may be further processed to yield a commercially attractive product.

The process of the present invention results in higher yields of isoprenoids, such as for instance CoQ10. The increase may be for instance at least about 10% compared to processes using a non-recombinant strain of for instance *Rhodobacter* or using a recombinant strain such as for instance *Rhodobacter* carrying the wild-type mev operon of e.g. a *Paracoccus* strain.

FIG. 1 represents the pathway for CoQ10 biosynthesis in *R. sphaeroides*, which uses the MEP pathway for IPP formation. The boxed region indicates the reaction sequence that comprises the mevalonate pathway (leading to formation of IPP), plus the IPP isomerase step. The mevalonate pathway does not naturally occur in *R. sphaeroides*. In *P. zeaxanthinifaciens*, the genes coding for the five enzymes of the mevalonate pathway plus IPP isomerase form an operon, called hereinafter the mevalonate operon.

The following Examples illustrate the invention without restricting it in any way.

EXAMPLE 1

Bacteria and Culture Conditions

*Rhodobacter sphaeroides* strain ATCC 35053 (obtained from the American Type Culture Collection, Manassas Va., USA) was used as the base host for construction of recombinant strains having improved production of CoQ10. All *R. sphaeroides* strains were grown at 30° C. in medium RS100. The composition and preparation of medium RS100 is summarized in Table 1. Fifty mg/l kanamycin was added to the medium for growth of recombinant strains. *E. coli* strains were grown at 37° C. in LB medium (Becton Dickinson, Sparks, Md., USA). For maintenance of plasmids in recombinant *E. coli* strains, ampicillin (100 mg/l) and/or kanamycin (25-50 mg/l, depending on the plasmid) were added to the culture medium. Liquid cultures of *E. coli* and *R. sphaeroides* were routinely grown aerobically in a rotary shaker at 200 rpm. When solid media were required, agar (1.5% final concentration) was added.

TABLE 1

Composition and preparation of medium RS100

| Medium RS100 | |
|---|---|
| Component | Amount (per liter distilled water) |
| Yeast extract | 10 g |
| Peptone | 10 g |
| NaCl | 0.5 g |
| $MgSO_4 \cdot 7H_2O$ | 0.5 g |
| D-glucose monohydrate | 33 g |

Components 1-5 are mixed together, the final volume is adjusted to 1 liter, and the pH is adjusted to 7.4 with 0.5 M NaOH. The resulting base medium is then sterilized by filtration through a 0.22 micron membrane. Two ml each of sterile Microelements solution and sterile CaFe solution (see below) are added to give the final medium RS100. For solid medium, components 1-5, plus 15 g agar, are first mixed together and autoclaved. After the medium is cooled down to about 60° C., the sterile microelements and CaFe solutions (2 ml of each) are added and the molten medium is mixed well and dispensed into sterile petri plates.

| Component | Amount per liter distilled water |
|---|---|
| Microelements solution | |
| $(NH_4)_2Fe(SO_4)_2 \cdot 6H_2O$ | 80 g |
| $ZnSO_4 \cdot 7H_2O$ | 6 g |
| $MnSO_4 \cdot H_2O$ | 2 g |
| $NiSO_4 \cdot 6H_2O$ | 0.2 g |
| EDTA | 6 g |
| CaFe solution | |
| $CaCl_2 \cdot 2H_2O$ | 75 g |
| $FeCl_3 \cdot 6H_2O$ | 5 g |
| HCl (37%) | 3.75 ml |

Sterilize by filtration through a 0.22 micron membrane, store at 4° C.

EXAMPLE 2

Analytical Assay for CoQ10

400 µl of whole cultivation broth (see Example 5) were transferred to a disposable 15 ml polypropylene centrifuge tube. 4 ml of stabilized extraction solution (0.5 g/l BHT in 1:1 (v/v) DMSO/THF) were added and the samples were mixed for 20 min in a laboratory shaker (IKA, Germany) to enhance extraction. Finally, the samples were centrifuged and the supernatants transferred to amber glass vials for analysis by reverse phase HPLC. This method was developed for the simultaneous determination of ubiquinones and their corresponding hydroquinones, with a clear separation of CoQ10 from the carotenoids phytoene, spheroidenone, spheroidene and neurosporene. Chromatography was performed using an Agilent 1100 HPLC system (Agilent Technologies, USA) equipped with a temperature-controlled autosampler and a diode array detector. The method parameters were as follows:

| Column | YMC Carotenoid C30 column |
| --- | --- |
| | 3 micron, steel, 150 mm × 3.0 mm I.D. |
| | (YMC, Part No. CT99S031503QT) |
| Guard column | Security Guard C18 (ODS, Octadecyl) |
| | 4 mm length × 3.0 mm I.D. |
| | (Phenomenex, Part No. AJO-4287) |
| Typical column pressure | 60 bar at start |
| Flow rate | 0.5 ml/min |
| Mobile phase | Mixture of |
| | acetonitrile(A):methanol(B):TBME(C) |
| Gradient profile | Time (min) %A %B %C |
| | 0     60  15  25 |
| | 13    60  15  25 |
| | 20    00  100 |
| | 22    60  15  25 |
| | 25    60  15  25 |
| Post time | 4 min. |
| Injection volume | 10 µl |
| Column temperature | 15° C. |
| Detection | Three wavelengths were used for detection |
| | of specific compounds according to |
| | Table 2 |

TABLE 2

HPLC retention times and wavelengths used

| Compound | Wavelength (nm) | Retention times (min) |
| --- | --- | --- |
| Phytoene | 280 | 7.9 |
| Ubiquinol-10 | 210 | 11.3 |
| CoQ10 | 210 | 12.6 |
| Spheroidenone (Z-isomers) | 450 | 10.6, 13.0, 14.6, 18.7 |
| E-Spheroidenone | 450 | 19.1 |
| E-Neurosporene | 450 | 20.4 |
| E-Spheroidene | 450 | 20.6 |

Calculations: Calculations were based on peak areas.

EXAMPLE 3

Cloning of Mutated Mev Operon from *P. zeaxanthinifaciens*

Construction of Plasmids pBBR-K-mev-op-wt and pBBR-K-mev-on-R114.

The construction of plasmid pBBR-K-mev-op-up-4 (plasmid containing the first 4 genes of the mevalonate operon) is described in detail in Example 13 (page 105, line 10 to page 106, line 8) of WO 02/099095.

Using *P. zeaxanthinifaciens* R114 genomic DNA as template, PCR is performed with primers hcs-5326 (SEQ ID NO:10) and mvd-9000 (SEQ ID NO:11). Primer hcs-5326 corresponds to the sequence of the *P. zeaxanthinifaciens* mev operon from nucleotide 3321 to 3340 of SEQ ID NO:2 while primer mvd-9000 corresponds to the reverse complement of the sequence from nucleotides 6977 to 6996 of SEQ ID NO:2.

The obtained PCR product of 3675 bp is cloned into pCR2.1-TOPO (Invitrogen, Carlsbad, Calif., USA), resulting into plasmid TOPO-pCR2.1-mev-op-d-3wt. This plasmid thus contains the downstream half of the mevalonate operon including the 3' end of hcs and the last three genes, mvk, pmk and mvd.

Plasmids pBBR-K-mev-op-up-4 and TOPO-pCR2.1-mev-op-d-3wt are digested with the restriction endonucleases SacI and NdeI and the resulting 3319 bp fragment from TOPO-pCR2.1-mev-op-d-3wt is ligated with the 8027 bp fragment from pBBR-K-mev-op-up-4. The resulting plasmid, pBBR-K-mev-op-R114, contains the complete mevalonate operon from *P. zeaxanthinifaciens* R114 including its (putative) promoter.

Construction of Plasmids pBBR-K-mev-op-wt-PcrtE-crtE and pBBR-K-mev-op-R114-PcrtE-crtE The construction of plasmid pBBR-K-PcrtE-crtE is described in detail in Example 6 (page 92, lines 10-17) of WO 02/099095. Plasmid pBBR-K-PcrtE-crtE was cut with NaeI and the 1.33 kb fragment was isolated and inserted into the Ecl136II site of pBBR-K-mev-op-up-4. The orientation of the insert was checked and the plasmid which carried the crtE gene in the same orientation as the mevalonate operon genes was designated pBBR-K-mev-op-up-4-PcrtE-crtE-2.

Plasmid pBBR-K-mev-op-up-4-PcrtE-crtE-2 was cut with SphI and SpeI and the resulting 5566 bp fragment containing the crtE gene was isolated. This fragment was ligated with the 7132 bp SphI-SpeI fragment obtained after a restriction digest of pBBR-K-mev-op-wt or pBBR-K-mev-op-R114 using the same enzymes, resulting in plasmid pBBR-K-mev-op-wt-PertE-crtE and pBBR-K-mev-op-R114-PcrtE-crtE, respectively.

Construction of Plasmids pBBR-K-mev-op-wt-PcrtE-ddsA$_{wt}$ and pBBR-K-mev-op-R114-PcrtE-ddsA$_{wt}$ The construction of plasmid pBBR-K-PcrtE is described in detail in Example 6 (page 91, lines 12-27) of WO 02/099095.

The ddsA gene from *P. zeaxanthinifaciens* strain ATCC 21588 (designated ddsA$_{wt}$) was amplified by PCR (GC-rich PCR System, Roche Molecular Biochemicals, Mannheim, Germany) using the primers dds-Nde (SEQ ID NO:12) and dds-Bam (SEQ ID NO:13) and cloned into pCR2.1-TOPO (Invitrogen, Carlsbad, Calif., USA) to result in plasmid TOPO-ddsA$_{wt}$.

Plasmid TOPO-ddsA$_{wt}$ was cut with NdeI and BamHI and the obtained fragment of 1005 bp containing the ddsA gene was cloned into plasmid pBBR-K-PcrtE cut with NdeI and BamHI, resulting in plasmid pBBR-K-PcrtE-ddsA$_{wt}$. A recognition site for the endonuclease EcoRI within the ddsA gene was eliminated by introducing a silent mutation with the QuikChange XL Site-Directed Mutagenesis Kit (Stratagene, La Jolla, Calif., USA) using the oligonucleotides dds-R-1 (SEQ ID NO:14) and dds-R-2 (SEQ ID NO:15). The resulting plasmid pBBR-K-PcrtE-ddsA$_{wt}$-R was cut with EcoRI and MamI and the fragment 1278 bp fragment containing the ddsA gene was inserted into TOPO-ddsA$_{wt}$ cut with EcoRI and EcoRV, resulting in the plasmid pCR2.1-TOPO-ddsA$_{wt}$-R. This plasmid was cut with Ce/II and XbaI and the obtained fragment of 1211 bp containing the ddsA gene was ligated with a 11.6 kb restriction fragment obtained from digestion of pBBR-K-mev-op-wt-PcrtE-crtE and pBBR-K-mev-op-R114-PcrtE-crtE, respectively, with Ce/II and BlnI. The resulting plasmids were named pBBR-K-mev-op-wt-PcdE-ddsA$_{wt}$ and pBBR-K-mev-op-R114-PcrtE-ddsA$_{wt}$, respectively.

Construction of Plasmid pBBR-K-mev-op-4-89-PcrtE-ddsA$_{wt}$

Plasmid pBBR-K-mev-op-4-89-PcrtE-ddsA$_{wt}$ is obtained by two rounds of PCR site-directed mutagenesis using the QuikChange XL Site-Directed Mutagenesis Kit (Stratagene, La Jolla, Calif., USA) and primers mut4-89-1-fw (SEQ ID NO:16) and mut4-89-1-rev (SEQ ID NO:17). Both primers are complementary to each other and contain the desired mutation A instead of C at position 2949 of SEQ ID NO:3, corresponding to position 268 of SEQ ID NO:4. The first mutagenesis reaction is set up as follows according to the manufacturer's instructions: 5 µl 10× reaction buffer, 10 ng plasmid DNA pBBR-K-mev-op-wt-PcrtE-ddsA$_{wt}$, 125 ng primer mut4-89-1-fw, 125 ng mut4-89-1-rev, 1 µl dNTP mix, 3 µl QuikSolution and 2.5 U PfuTurbo DNA polymerase are mixed in a final volume of 50 µl. The cycling is carried out by using the following parameters: 1 cycle: 95° C. for 1 min; 18 cycles: 95° C. for 50 sec, 60° C. for 50 sec, 68° C. for 30 min; 1 cycle: 68° C. for 7 min. After cooling the reaction mix to 37° C., 10 U of the restriction endonuclease DpnI is added and the reaction is incubated at 37° C. for 2 hours. Escherichia coli XL10-Gold Ultracompetent cells (Stratagene, La Jolla, Calif., USA) are transformed with the DpnI-treated DNA according to the manufacturer's protocol.

The resulting plasmid pBBR-K-mev-op-4-89-1-PcrtE-ddsA$_{wt}$ is isolated and used as template DNA for a second round of PCR site-directed mutagenesis using the primers mut4-89-2-fw (SEQ ID NO:18) and mut4-89-2-rev (SEQ ID NO:19) which contain the desired mutation C instead of T at position 6948 of SEQ ID NO:3. The mutagenesis is carried out as described above. The obtained plasmid pBBR-K-mev-op-4-89-PcrtE-ddsA$_{wt}$ was isolated and sequenced at Microsynth GmbH (Balgach, Switzerland). The complete sequence of the mutated mev operon is represented in SEQ ID NO:3, comprising the following genes: mvaA (encoding the hydroxymethylglutaryl-CoA reductase) on position 617 to 1639, idi (encoding the isopentenyl diphosphate isomerase) on position 1636 to 2685, hcs (encoding the hydroxymethyl-glutaryl-CoA synthase) on position 2682 to 3848, mvk (encoding the mevalonate kinase) on position 3829 to 4965, pmk (encoding the phosphomevalonate kinase) on position 4965 to 5882, and mvd (encoding the diphosphomevalonate decarboxylase) on position 5875 to 6873.

EXAMPLE 4

Introduction of the Mutated Mev Operon into R. sphaeroides ATCC 35053

Transformation of E. coli S17-1 (Simon et al., Bio/Technology 11, 784-791, 1983) with plasmids carrying the mutated mev operon and subsequent transfer of plasmids from E. coli S17-1 to R. sphaeroides ATCC 35053 by conjugation were performed using standard procedures (Nishimura et al., Nucl. Acids Res. 18, 6169, 1990; Simon et al., Bio/Technology 1983, 784-91).

A spontaneous rifampicin resistant mutant of R. sphaeroides ATCC 35053 was first isolated by growing strain ATCC 35053 in RS100 liquid medium supplemented with 100 mg/l rifampicin, plating the cells on RS100 plates containing 100 mg/l rifampicin, and isolating a single colony. For the conjugation, one milliliter aliquots of cultures of the recipient cells (rifampicin-resistant R. sphaeroides ATCC 35053) grown in RS100 medium containing 100 mg/l rifampicin and the donor cells (E. coli S17-1 carrying the plasmid to be transferred, grown in LB broth containing 50 mg/l kanamycin) were pelleted by centrifugation. The supernatant was discarded, and the cells were washed twice with fresh RS100 medium to remove antibiotics. Each pellet was then resuspended in 1 ml of fresh RS100 medium. Fifty microliters of donor cells and 0.45 ml of recipient cells were mixed, pelleted by centrifugation, resuspended in 0.03 ml of fresh RS100 medium and spotted onto an RS100 plate. After overnight incubation at 30° C. the cells were harvested with an inoculating loop and resuspended in 0.3 ml of RS100 medium. Dilutions of this suspension were spread onto RS100 plates containing 100 mg/l rifampicin and 50 mg/l kanamycin and incubated at 30° C. Colonies (putative transformed cells of R. sphaeroides ATCC 35053) were picked from the plates, grown in liquid RS100 medium containing 50 mg/l kanamycin and the presence of the plasmid was tested in a PCR reaction with an annealing temperature of 56° C. and an elongation time of 1 min, 15 sec using the following two different primer pairs:

pBBR-K-up (SEQ ID NO:20)/PcrtE-2442 (SEQ ID NO:21)

Kan3out (SEQ ID NO:22)/mvaA3256 (SEQ ID NO:23)

Positive clones were streaked onto RS100 plates containing 50 mg/l kanamycin to obtain single colonies. One single colony from each clone was again grown in liquid RS100 medium containing 50 mg/l kanamycin, and the presence of the expected plasmid was confirmed by PCR as described above. The resulting recombinant strain was named ATCC 35053/pBBR-K-mev-op-4-89-PcrtE-ddsA$_{wt}$.

EXAMPLE 5

Production of CoQ10 in Transformed Strains of R. sphaeroides ATCC 35053

R. sphaeroides strains ATCC 35053, ATCC 35053/pBBR-K-mev-op-R114-PcrtE-ddsA$_{wt}$ and ATCC 35053/pBBR-K-mev-op-4-89-PcrtE-ddsA$_{wt}$ were grown in shake flask cultures in RS100 medium. Cultures containing the recombinant R. sphaeroides contained 50 mg/l kanamycin. Twenty five-milliliter cultures were grown at 30° C. in 250-ml baffled Erlenmeyer flasks with shaking at 200 rpm. For testing CoQ10 production, frozen glycerolized stock cultures of the R. sphaeroides strains were used to inoculate 25-ml seed cultures. After growth of the seed cultures for 24-28 hours, suitable volumes of the cultures were used to inoculate the experimental flasks such that the initial optical density at 660 nanometers (OD$_{660}$) was 0.16. Two milliliter samples were taken aseptically at 24 hour intervals. Analyses included growth (measured as OD660), pH, glucose in the culture supernatant and CoQ10 and carotenoids (determined by HPLC) as described in Example 2. The results are summarized in Table 3. These results clearly show that the expression of the cloned mutated mevalonate operon from P. zeaxanthinifaciens significantly improved CoQ10 production in R. sphaeroides.

TABLE 3

Production of CoQ10 in transformed R. sphaeroides ATCC 35053 strains

| Strain | Time (hr) | CoQ10 mg/l | Specific Formation[1] |
|---|---|---|---|
| ATCC 35053 | 24 | 34.4 | 1.2 |
| ATCC 35053/pBBR-K-mev-op-R114-PcrtE-ddsA$_{wt}$ | 24 | 49.5 | 2.1 |

TABLE 3-continued

Production of CoQ10 in transformed *R. sphaeroides* ATCC 35053 strains

| Strain | Time (hr) | CoQ10 mg/l | Specific Formation[1] |
|---|---|---|---|
| ATCC 35053/pBBR-K-mev-op-4-89-PcrtE-ddsA$_{wt}$ | 24 | 57.7 | 2.3 |
| ATCC 35053 | 48 | 56.0 | 2.0 |
| ATCC 35053/pBBR-K-mev-op-R114-PcrtE-ddsA$_{wt}$ | 48 | 128.4 | 3.8 |
| ATCC 35053/pBBR-K-mev-op-4-89-PcrtE-ddsA$_{wt}$ | 48 | 148.9 | 4.4 |
| ATCC 35053 | 72 | 62.3 | 2.2 |
| ATCC 35053/pBBR-K-mev-op-R114-PcrtE-ddsA$_{wt}$ | 72 | 150.3 | 4.6 |
| ATCC 35053/pBBR-K-mev-op-4-89-PcrtE-ddsA$_{wt}$ | 72 | 166.4 | 5.0 |

[1]Specific Formation is expressed as mg/l CoQ10 produced/OD$_{660}$.

The invention claimed is:

1. An isolated polynucleotide comprising genes encoding a protein having hydroxymethylglutaryl-CoA reductase activity, isopentenyl diphosphate isomerase activity, hydroxymethylglutaryl-CoA synthase activity, mevalonate kinase activity, phosphomevalonate kinase activity, and diphosphomevalonate decarbo-xylase activity, wherein said polynucleotide comprises a nucleotide sequence selected from the group consisting of nucleotide sequences obtainable from SEQ ID NO:1 or 2 by mutating the cytosine at position 2949 to adenine and/or the thymidine at position 6948 to cytosine.

2. An isolated polynucleotide comprising SEQ ID NO:3 or a fragment thereof, wherein the polynucleotide encodes a protein having hydroxymethylglutaryl-CoA synthase activity.

3. The polynucleotide according to claim 2 comprising SEQ ID NO:3.

4. An isolated polynucleotide selected from the group consisting of:
   (a) polynucleotides encoding a polypeptide comprising the amino acid sequence of SEQ ID NO:7 and
   (b) polynucleotides comprising the nucleotide sequence of SEQ ID NO:6.

5. A recombinant microorganism comprising a polynucleotide according to claim 1.

6. A process for the production of isoprenoids comprising:
   (a) introducing a polynucleotide according to claim 1 into a microorganism which is originally deficient in hydroxymethylglutaryl-CoA synthase activity, and
   (b) cultivating the microorganism of step (a) under conditions to produce isoprenoids.

7. The process according to claim 6 wherein the microorganism in which the polynucleotide is introduced is selected from the group consisting of microorganisms belonging to the genus *Rhodobacter*.

8. The microorganism according to claim 5 further comprising a polynucleotide selected from the group consisting of:
   (a) polynucleotides encoding a polypeptide comprising the amino acid sequence of SEQ ID NO:9 and
   (b) polynucleotides comprising the nucleotide sequence of SEQ ID NO:8.

9. The microorganism according to claim 5 which is selected from the group consisting of microorganisms belonging to the genus *Rhodobacter*.

10. A process of using a microorganism according to claim 5, comprising cultivating the microorcianism under conditions to produce isoprenoids.

11. The process according to claim 6 wherein the isoprenoids comprise coenzyme Q10.

12. The process according to claim 7 wherein the microorganism belongs to the species *R. sphaeroides*.

13. The microorganism according to claim 9 wherein the microorganism belongs to the species *R. sphaeroides*.

14. The process according to claim 10 wherein the isoprenoids comprise coenzyme Q10.

15. The polynucleotide according to claim 1 which is comprised of SEQ ID NO:1 obtainable by mutating the cytosine at position 2949 to adenine and/or the thymidine at position 6948 to cytosine.

16. The polynucleotide according to claim 1 which is comprised of SEQ ID NO: 2 obtainable by mutating the cytosine at position 2949 to adenine and/or the thymidine at position 6948 to cytosine.

17. A process for the production of isoprenoids comprising:
(a) introducing a polynucleotide according to claim 2 into a microorganism which is originally deficient in hydroxymethylglutaryl-CoA synthase activity, and
(b) cultivating the microorganism of step (a) under conditions to produce isoprenoids.

18. A recombinant microorganism comprising a polynucleotide according to claim 2.

19. A process of using a microorganism according to claim 18, comprising cultivating the microorganism under conditions to produce isoprenoids.

20. A process for the production of isoprenoids comprising:
(a) introducing a polynucleotide according to claim 4 into a microorganism which is originally deficient in hydroxymethylglutaryl-CoA synthase activity, and
(b) cultivating the microorganism of step (a) under conditions to produce isoprenoids.

21. A recombinant microorganism comprising a polynucleotide according to claim 4.

22. A process of using a microorganism according to claim 21, comprising cultivating the microorganism under conditions to produce isoprenoids.

23. A process of using a microorganism according to claim 8, comprising cultivating the microorganism under conditions to produce isoprenoids.

* * * * *

SEQUENCE LISTING

<160> NUMBER OF SEQ ID NOS: 23

<210> SEQ ID NO 1
<211> LENGTH: 7096
<212> TYPE: DNA
<213> ORGANISM: Paracoccus zeaxanthinifaciens ATCC 21588

<400> SEQUENCE: 1

```
cggctgggtg tggcggaccg ctatcaggac atagcgttgg ctacccgtga tattgctgaa      60
gagcttggcg gcgaatgggc tgaccgcttc ctcgtgcttt acggtatcgc cgctcccgat     120
tcgcagcgca tcgccttcta tcgccttctt gacgagttct tctgagcggg actctggggt     180
tcgaaatgac cgaccaagcg acgcccaacc tgccatcacg agatttcgat tccaccgccg     240
ccttctatga aaggttgggc ttcggaatcg ttttccggga cgccggctgg atgatcctcc     300
agcgcgggga tctcatgctg gagttcttcg cccaccccca tgggcaaata ttatacgcaa     360
ggcgacaagg tgctgatgcc gctggcgatt caggttcatc atgccgtttg tgatggcttc     420
catgtcggca gaatgcttaa tgaattacaa cagtttttat gcaacgcgtc gaaccgcccg     480
tccgacgccg gtttccgcac ggaaacgcgc ggcaagttga cataacttgc acgcgacgtc     540
tcgattctgc ccgcgaagaa tgcgatgcat ccagatgatg cagaacgaag aagcggaagc     600
gcccgtgaaa gaccagatga tttcccatac cccggtgccc acgcaatggg tcggcccgat     660
cctgttccgc ggccccgtcg tcgagggccc gatcagcgcg ccgctggcca cctacgagac     720
gccgctctgg ccctcgaccg cgcgggggggc aggggttttcc cggcattcgg gcgggatcca     780
ggtctcgctg gtcgacgaac gcatgagccg ctcgatcgcg ctgcgggcgc atgacggggc     840
ggcggcgacc gccgcctggc agtcgatcaa ggcccgccag gaagaggtcg cggccgtggt     900
cgccaccacc agccgcttcg cccgccttgt cgagctgaat cgccagatcg tgggcaacct     960
gctttacatc cgcatcgaat gcgtgacggg cgacgcctcg ggtcacaaca tggtcaccaa    1020
ggccgccgag gccgtgcagg gctggatcct gtcggaatac ccgatgctgg cctattccac    1080
gatctcgggg aacctgtgca ccgacaagaa ggcgtcggcg gtcaacggca tcctgggccg    1140
cggcaaatac gccgtcgccg aggtcgagat cccgcgcaag atcctgaccc gcgtgctgcg    1200
caccagcgcc gagaagatgg tccgcctgaa ctacgagaag aactatgtcg ggggtacgct    1260
ggcggggtcg ctgcgcagtg cgaacgcgca tttcgccaac atgctgctgg gcttctacct    1320
ggcgacgggg caggacgcgg ccaacatcat cgaggccagc cagggcttcg tccattgcga    1380
```

-continued

```
ggcccgcggc gaggatctgt atttctcgtg cacgctgccc aacctcatca tgggctcggt    1440
cggtgccggc aagggcatcc cctcgatcga ggagaacctg tcgcggatgg gctgccgcca    1500
gccgggcgaa cccggcgaca cgcgcgccg tcttgcggcg atctgcgcgg gcgtcgtgct    1560
gtgtggtgaa ttgtcgctgc ttgcggccca gaccaacccc ggagagttgg tccgcaccca    1620
catggagatg gagcgatgac cgacagcaag gatcaccatg tcgcggggcg caagctggac    1680
catctgcgtg cattggacga cgatgcggat atcgaccggg gcgacagcgg cttcgaccgc    1740
atcgcgctga cccatcgcgc cctgcccgag gtggatttcg acgccatcga cacggcgacc    1800
agcttcctgg gccgtgaact gtccttcccg ctgctgatct cgtccatgac cggcggcacc    1860
ggcgaggaga tcgagcgcat caaccgcaac ctggccgctg gtgccgagga ggcccgcgtc    1920
gccatggcgg tgggctcgca gcgcgtgatg ttcaccgacc cctcggcgcg ggccagcttc    1980
gacctgcgcg cccatgcgcc caccgtgccg ctgctggcca atatcggcgc ggtgcagctg    2040
aacatggggc tggggctgaa ggaatgcctg gccgcgatcg aggtgctgca ggcggacggc    2100
ctgtatctgc acctgaaccc cctgcaagag gccgtccagc ccgaggggga tcgcgacttt    2160
gccgatctgg gcagcaagat cgcggccatc gcccgcgacg ttcccgtgcc cgtcctgctg    2220
aaggaggtgg gctgcggcct gtcggcggcc gatatcgcca tcgggctgcg cgccgggatc    2280
cggcatttcg acgtggccgg tcgcggcggc acatcctgga gccggatcga gtatcgccgc    2340
cgccagcggg ccgatgacga cctgggcctg gtcttccagg actggggcct gcagaccgtg    2400
gacgccctgc gcgaggcgcg gcccgcgctt gcggcccatg atggaaccag cgtgctgatc    2460
gccagcggcg gcatccgcaa cggtgtcgac atggcgaaat gcgtcatcct gggggccgac    2520
atgtgcgggg tcgccgcgcc cctgctgaaa gcggcccaaa actcgcgcga ggcggttgta    2580
tccgccatcc ggaaactgca tctggagttc cggacagcca tgttcctcct gggttgcggc    2640
acgcttgccg acctgaagga caattcctcg cttatccgtc aatgaaagtg cctaagatga    2700
ccgtgacagg aatcgaagcg atcagcttct acaccccca gaactacgtg ggactggata    2760
tccttgccgc gcatcacggg atcgaccccg agaagttctc gaaggggatc gggcaggaga    2820
aaatcgcact gcccggccat gacgaggata tcgtgaccat ggccgccgag gccgcgctgc    2880
cgatcatcga acgcgcgggc acgcagggca tcgacacggt tctgttcgcc accgagagcg    2940
ggatcgacca gtcgaaggcc gccgccatct atctgcgccg cctgctggac ctgtcgccca    3000
actgccgttg cgtcgagctg aagcaggcct gctattccgc gacggcgcg ctgcagatgg    3060
cctgcgcgca tgtcgcccgc aagcccgacc gcaaggtgct ggtgatcgcg tccgatgtcg    3120
cgcgctatga ccgcgaaagc tcgggcgagg cgacgcaggg tgcgggcgcc gtcgccatcc    3180
ttgtcagcgc cgatcccaag gtggccgaga tcggcaccgt ctcggggctg ttcaccgagg    3240
atatcatgga tttctggcgg ccgaaccacc gccgcacgcc cctgttcgac ggcaaggcat    3300
cgacgctgcg ctatctgaac gcgctggtcg aggcgtggaa cgactatcgc gcgaatggcg    3360
gccacgagtt cgccgatttc gcgcatttct gctatcacgt gccgttctcg cggatgggcg    3420
agaaggcgaa cagccacctg gccaaggcga acaagacgcc ggtggacatg gggcaggtgc    3480
agacgggcct gatctacaac cggcaggtcg ggaactgcta taccgggtcg atctacctgg    3540
cattcgcctc gctgctggag aacgctcagg aggacctgac cggcgcgctg gtcggtctgt    3600
tcagctatgg ctcgggtgcg acgggcgaat tcttcgatgc gcggatcgcg cccggttacc    3660
gcgaccacct gttcgcggaa cgccatcgcg aattgctgca ggatcgcacg cccgtcacat    3720
atgacgaata cgttgccctg tgggacgaga tcgacctgac gcagggcgcg cccgacaagg    3780
```

```
cgcgcggtcg tttcaggctg gcaggtatcg aggacgagaa gcgcatctat gtcgaccggc    3840
aggcctgaag caggcgccca tgccccgggc aagctgatcc tgtccgggga acattccgtg    3900
ctctatggtg cgcccgcgct tgccatggcc atcgcccgct ataccgaggt gtggttcacg    3960
ccgcttggca ttggcgaggg gatacgcacg acattcgcca atctctcggg cggggcgacc    4020
tattcgctga agctgctgtc ggggttcaag tcgcggctgg accgccggtt cgagcagttc    4080
ctgaacggcg acctaaaggt gcacaaggtc ctgacccatc ccgacgatct ggcggtctat    4140
gcgctggcgt cgcttctgca cgacaagccc cggggaccg ccgcgatgcc gggcatcggc     4200
gcgatgcacc acctgccgcg accgggtgag ctgggcagcc ggacggagct gcccatcggc    4260
gcgggcatgg ggtcgtctgc ggccatcgtc gcggccacca cggtcctgtt cgagacgctg    4320
ctggaccggc ccaagacgcc cgaacagcgc ttcgaccgcg tccgcttctg cgagcggttg    4380
aagcacggca aggccggtcc catcgacgcg gccagcgtcg tgcgcggcgg gcttgtccgc    4440
gtgggcggga acgggccggg ttcgatcagc agcttcgatt tgcccgagga tcacgacctt    4500
gtcgcgggac gcggctggta ctgggtactg cacgggcgcc ccgtcagcgg gaccggcgaa    4560
tgcgtcagcg cggtcgcggc ggcgcatggt cgcgatgcgg cgctgtggga cgccttcgca    4620
gcctgcaccc gcgcgttgga ggccgcgctg ctgtctgggg gcagccccga cgccgccatc    4680
accgagaacc agcgcctgct ggaacgcatc ggcgtcgtgc cggcagcgac gcaggccctc    4740
gtggcccaga tcgaggaggc gggtggcgcg gccaagatct gcggcgcagg ttccgtgcgg    4800
ggcgatcacg gcggggcggt cctcgtgcgg attgacgacg cgcaggcgat ggcttcggtc    4860
atggcgcgcc atcccgacct cgactgggcg cccctgcgca tgtcgcgcac ggggggcgga    4920 cccgccccg cgccgcgtgc gcaaccgctg ccggggcagg gctgatgat caggtcatcc      4980 gcgccagcgc gccgggttcg gtcatgatca cgggcgaaca tgccgtggtc tatggacacc    5040
gcgccatcgt cgccgggatc gagcagcgcg cccatgtgac gatcgtcccg cgtgccgacc    5100
gcatgtttcg catcacctcg cagatcgggg cgccgcagca ggggtcgctg acgatctgc     5160 ctgcgggcgg gacctatcgc ttcgtgctgg ccgccatcgc gcgacacgcg ccggacctgc    5220
cttgcgggtt cgacatggac atcaccctcg ggatcgatcc gaggctcggg cttggatcct    5280
cggcggcggt gacggtcgcc tgcctcggcg cgctgtcgcg gctggcgggg cggggaccg    5340 aggggctgca tgacgacgcg ctgcgcatcg tccgcgccat ccagggcagg ggcagcgggg    5400
ccgatctggc ggccagcctg catggcggct tcgtcgccta tcgcgcgccc gatggcggtg    5460
ccgcgcagat cgaggcgctt ccggtgccgc cggggccgtt cggcctgcgc tatgcgggct    5520
acaagacccc gacagccgag gtgctgcgcc ttgtggccga tcggatggcg ggcaacgagg    5580
ccgctttcga cgcgctctac tcccggatgg gcgcaagcgc agatgccgcg atccgcgcgg    5640
cgcaagggct ggactgggct gcattccacg acgcgctgaa cgaataccag cgcctgatgg    5700
agcagctggg cgtgtccgac gacacgctgg acgcgatcat ccgcgaggcg cgcgacgcgg    5760
gcgccgcagt cgccaagatc tccggctcgg ggctggggga ttgcgtgctg cactgggcg    5820 accagcccaa gggtttcgtg cccgcaagca ttgccgagaa gggacttgtt ttcgatgact    5880
gatgccgtcc gcgacatgat cgccgtgcc atggcgggcg cgaccgacat ccagcagcc     5940 gaggcttatg cgcccagcaa catcgcgctg tcgaaatact ggggcaagcg cgacgccgcg    6000
cggaaccttc cgctgaacag ctccgtctcg atctcgttgg cgaactgggg ctctcatacg    6060
cgggtcgagg ggtccggcac gggccacgac gaggtgcatc acaacggcac gctgctggat    6120
```

```
ccgggcgacg ccttcgcgcg ccgcgcgttg gcattcgctg acctgttccg ggggggagg      6180 cacctgccgc tgcggatcac gacgcagaac tcgatcccga cggcgcggg gcttgcctcg      6240 tcggcctcgg ggttcgcggc gctgacccgt gcgctggcgg gggcgttcgg gctggatctg      6300
gacgacacgg atctgagccg catcgcccgg atcggcagtg gcagcgccgc ccgctcgatc      6360
tggcacggct tcgtccgctg gaaccggggc gaggccgagg atgggcatga cagccacggc      6420
gtcccgctgg acctgcgctg gcccggcttc cgcatcgcga tcgtggccgt ggacaagggg      6480
cccaagcctt tcagttcgcg cgacggcatg aaccacacgg tcgagaccag cccgctgttc      6540
ccgccctggc ctgcgcaggc ggaagcggat tgccgcgtca tcgaggatgc gatcgccgcc      6600
cgcgacatgg ccgccctggg tccgcgggtc gaggcgaacg cccttgcgat gcacgccacg      6660
atgatggccg cgcgcccgcc gctctgctac ctgacgggcg gcagctggca ggtgctggaa      6720
cgcctgtggc aggcccgcgc ggacgggctt gcggcctttg cgacgatgga tgccggcccg      6780
aacgtcaagc tgatcttcga ggaaagcagc ccgccgacg tgctgtacct gttcccccgac      6840 gccagcctga tcgcgccgtt cgaggggcgt tgaacgcgta agacgaccac tgggtaaggt      6900
tctgccgcgc gtggtctcga ctgcctgcaa agaggtgctt gagttgctgc gtgactgcgg      6960
cggccgactt cgtgggactt gcccgccacg ctgacgaagg gcgaattcca gcacactggc      7020
ggccgttact agttctagag cggccgccac cgcggtggag ggcggcacct cgctaacgga      7080
ttcaccgttt ttatca                                                     7096

<210> SEQ ID NO 2
<211> LENGTH: 7096
<212> TYPE: DNA
<213> ORGANISM: Paracoccus sp. R114

<400> SEQUENCE: 2
cggctgggtg tggcggaccg ctatcaggac atagcgttgg ctacccgtga tattgctgaa        60
gagcttggcg gcgaatgggc tgaccgcttc ctcgtgcttt acggtatcgc cgctcccgat       120
tcgcagcgca tcgccttcta tcgccttctt gacgagttct tctgagcggg actctggggt       180
tcgaaatgac cgaccaagcg acgcccaacc tgccatcacg agatttcgat tccaccgccg       240
ccttctatga aaggttgggc ttcggaatcg ttttccggga cgccggctgg atgatcctcc       300
agcgcgggga tctcatgctg gagttcttcg cccaccccca tgggcaaata ttatacgcaa       360
ggcgacaagg tgctgatgcc gctggcgatt caggttcatc atgccgtttg tgatggcttc       420
catgtcggca gaatgcttaa tgaattacaa cagttttat gcaacgcgtc gaaccgcccg       480
tccgacgccg gtttccgcac ggaaacgcgc ggcaagttga cataacttgc acgcgacgtc       540
tcgattctgc ccgcgaagaa tgcgatgcat ccagatgatg cagaacgaag aagcggaagc       600
gcccgtgaaa gaccagatga tttcccatac cccggtgccc acgcaatggg tcggcccgat       660
cctgttccgc ggccccgtcg tcgagggccc gatcagcgcg ccgctggcca cctacgagac       720
gccgctctgg ccctcgaccg cgcgggggc aggggtttcc cggcattcgg gcgggatcca       780
ggtctcgctg gtcgacgaac gcatgagccg ctcgatcgcg ctgcgggcgc atgacggggc       840
ggcggcgacc gccgcctggc agtcgatcaa ggcccgccag gaagaggtcg cggccgtggt       900
cgccaccacc agccgcttcg cccgccttgt cgagctgaat cgccagatcg tgggcaacct       960
gctttacatc cgcatcgaat gcgtgacggg cgacgcctcg ggtcacaaca tggtcaccaa      1020
ggccgccgag gccgtgcagg gctggatcct gtcggaatac ccgatgctgg cctattccac      1080
gatctcgggg aacctgtgca ccgacaagaa ggcgtcggcg gtcaacggca tcctgggccg      1140
```

```
cggcaaatac gccgtcgccg aggtcgagat cccgcgcaag atcctgaccc gcgtgctgcg   1200
caccagcgcc gagaagatgg tccgcctgaa ctacgagaag aactatgtcg ggggtacgct   1260
ggcggggtcg ctgcgcagtg cgaacgcgca tttcgccaac atgctgctgg gcttctacct   1320
ggcgacgggg caggacgcgg ccaacatcat cgaggccagc cagggcttcg tccattgcga   1380
ggcccgcggc gaggatctgt atttctcgtg cacgctgccc aacctcatca tgggctcggt   1440
cggtgccggc aagggcatcc cctcgatcga ggagaacctg tcgcgatgg gctgccgcca   1500 gccgggcgaa cccggcgaca acgcgcgccg tcttgcggcg atctgcgcgg gcgtcgtgct   1560
gtgtggtgaa ttgtcgctgc ttgcggccca gaccaacccc ggagagttgg tccgcaccca   1620
catggagatg gagcgatgac cgacagcaag gatcaccatg tcgcggggcg caagctggac   1680
catctgcgtg cattggacga cgatgcggat atcgaccggg gcgacagcgg cttcgaccgc   1740
atcgcgctga cccatcgcgc cctgcccgag gtggatttcg acgccatcga cacggcgacc   1800
agcttcctgg gccgtgaact gtccttcccg ctgctgatct cgtccatgac cggcggcacc   1860
ggcgaggaga tcgagcgcat caaccgcaac ctggccgctg gtgccgagga ggcccgcgtc   1920
gccatggcgg tgggctcgca gcgcgtgatg ttcaccgacc cctcggcgcg ggccagcttc   1980
gacctgcgcg cccatgcgcc caccgtgccg ctgctggcca atatcggcgc ggtgcagctg   2040
aacatggggc tggggctgaa ggaatgcctg gccgcgatcg aggtgctgca ggcggacggc   2100
ctgtatctgc acctgaaccc cctgcaagag gccgtccagc ccgaggggga tcgcgacttt   2160
gccgatctgg gcagcaagat cgcggccatc gcccgcgacg ttcccgtgcc cgtcctgctg   2220
aaggaggtgg gctgcggcct gtcggcggcc gatatcgcca tcgggctgcg cgccgggatc   2280
cggcatttcg acgtggccgg tcgcggcggc acatcctgga gccggatcga gtatcgccgc   2340
cgccagcggg ccgatgacga cctgggcctg gtcttccagg actggggcct gcagaccgtg   2400
gacgccctgc gcgaggcgcg gcccgcgctt gcggcccatg atggaaccag cgtgctgatc   2460
gccagcggcg gcatccgcaa cggtgtcgac atggcgaaat gcgtcatcct gggggccgac   2520
atgtgcgggg tcgccgcgcc cctgctgaaa gcggcccaaa actcgcgcga ggcggttgta   2580
tccgccatcc ggaaactgca tctggagttc cggacagcca tgttcctcct gggttgcggc   2640
acgcttgccg acctgaagga caattcctcg cttatccgtc aatgaaagtg cctaagatga   2700
ccgtgacagg aatcgaagcg atcagcttct acacccccca gaactacgtg ggactggata   2760
tccttgccgc gcatcacggg atcgaccccg agaagttctc gaaggggatc gggcaggaga   2820
aaatcgcact gcccggccat gacgaggata tcgtgaccat ggccgccgag gccgcgctgc   2880
cgatcatcga acgcgcgggc acgcagggca tcgacacggt tctgttcgcc accgagagcg   2940
ggatcgacca gtcgaaggcc gccgccatct atctgcgccg cctgctggac ctgtcgccca   3000
actgccgttg cgtcgagctg aagcaggcct gctattccgc gacggcggcg ctgcagatgg   3060
cctgcgcgca tgtcgcccgc aagcccgacc gcaaggtgct ggtgatcgcg tccgatgtcg   3120
cgcgctatga ccgcgaaagc tcgggcgagg cgacgcaggg tgcggcgcc gtcgccatcc   3180 ttgtcagcgc cgatcccaag gtggccgaga tcggcaccgt ctcggggctg ttcaccgagg   3240
atatcatgga tttctggcgg ccgaaccacc gccgcacgcc cctgttcgac ggcaaggcat   3300
cgacgctgcg ctatctgaac gcgctggtcg aggcgtggaa cgactatcgc gcgaatggcg   3360
gccacgagtt cgccgatttc gcgcatttct gctatcacgt gccgttctcg cggatgggcg   3420
agaaggcgaa cagccacctg gccaaggcga acaagacgcc ggtggacatg gggcaggtgc   3480
```

-continued

```
agacgggcct gatctacaac cggcaggtcg ggaactgcta taccgggtcg atctacctgg   3540
cattcgcctc gctgctggag aacgctcagg aggacctgac cggcgcgctg gtcggtctgt   3600
tcagctatgg ctcgggtgcg acgggcgaat tcttcgatgc gcggatcgcg cccggttacc   3660
gcgaccacct gttcgcggaa cgccatcgcg aattgctgca ggatcgcacg cccgtcacat   3720
atgacgaata cgttgccctg tgggacgaga tcgacctgac gcaggcgcgc cccgacaagg   3780
cgcgcggtcg tttcaggctg gcaggtatcg aggacgagaa gcgcatctat gtcgaccggc   3840
aggcctgaag caggcgccca tgccccgggc aagctgatcc tgtccgggga acattccgtg   3900
ctctatggtg cgcccgcgct tgccatggcc atcgcccgct ataccgaggt gtggttcacg   3960
ccgcttggca ttggcgaggg gatacgcacg acattcgcca atctctcggg cggggcgacc   4020
tattcgctga agctgctgtc gggggttcaag tcgcggctgg accgccggtt cgagcagttc   4080
ctgaacggcg acctaaaggt gcacaaggtc ctgacccatc ccgacgatct ggcggtctat   4140
gcgctggcgt cgcttctgca cgacaagccc cggggaccg ccgcgatgcc gggcatcggc    4200
gcgatgcacc acctgccgcg accgggtgag ctgggcagcc ggacggagct gcccatcggc   4260
gcgggcatgg ggtcgtctgc ggccatcgtc gcggccacca cggtcctgtt cgagacgctg   4320
ctggaccggc ccaagacgcc cgaacagcgc ttcgaccgcg tccgcttctg cgagcggttg   4380
aagcacggca aggccggtcc catcgacgcg gccagcgtcg tgcgcggcgg gcttgtccgc   4440
gtgggcggga acgggccggg ttcgatcagc agcttcgatt tgcccgagga tcacgacctt   4500
gtcgcgggac gcggctggta ctgggtactg cacgggcgcc ccgtcagcgg gaccggcgaa   4560
tgcgtcagcg cggtcgcggc ggcgcatggt cgcgatgcgg cgctgtggga cgccttcgca   4620
gtctgcaccc gcgcgttgga ggccgcgctg ctgtctgggg gcagccccga cgccgccatc   4680
accgagaacc agcgcctgct ggaacgcatc ggcgtcgtgc cggcagcgac gcaggccctc   4740
gtggcccaga tcgaggaggc gggtggcgcg gccaagatct gcggcgcagg ttccgtgcgg   4800
ggcgatcacg gcggggcggt cctcgtgcgg attgacgacg cgcaggcgat ggcttcggtc   4860
atggcgcgcc atcccgacct cgactgggcg cccctgcgca tgtcgcgcac ggggcggca   4920 cccggccccg cgccgcgtgc gcaaccgctg ccggggcagg gctgatggat caggtcatcc   4980
gcgccagcgc gccgggttcg gtcatgatca cgggcgaaca tgccgtggtc tatgacacc   5040 gcgccatcgt cgccgggatc gagcagcgcg cccatgtgac gatcgtcccg cgtgccgacc   5100
gcatgtttcg catcacctcg cagatcgggg cgccgcagca ggggtcgctg gacgatctgc   5160
ctgcgggcgg gacctatcgc ttcgtgctgg ccgccatcgc gcgacacgcg ccggacctgc   5220
cttgcgggtt cgacatggac atcacctcgg ggatcgatcc gaggctcggg cttggatcct   5280
cggcggcggt gacggtcgcc tgcctcgcg cgctgtcgcg gctggcgggg cggggaccg    5340 agggcgctgca tgacgacgcg ctgcgcatcg tccgcgccat ccagggcagg ggcagcgggg   5400
ccgatctggc ggccagcctg catggcggct tcgtcgccta tcgcgcgccc gatggcggtg   5460
ccgcgcagat cgaggcgctt ccggtgccgc cggggccgtt cggcctgcgc tatgcgggct   5520
acaagacccc gacagccgag gtgctgcgcc ttgtggccga tcggatggcg ggcaacgagg   5580
ccgctttcga cgcgctctac tcccggatgg gcgcaagcgc agatgccgcg atccgcgcgg   5640
cgcaagggct ggactgggct gcattccacg acgcgctgaa cgaataccag cgcctgatgg   5700
agcagctggg cgtgtccgac gacacgctgg acgcgatcat ccgcgaggcg cgcgacgcgg   5760
gcgccgcagt cgccaagatc tccggctcgg ggctggggga ttgcgtgctg cactgggcg   5820 accagcccaa gggtttcgtg cccgcaagca ttgccgagaa gggacttgtt ttcgatgact   5880
```

-continued

| | |
|---|---|
| gatgccgtcc gcgacatgat cgcccgtgcc atggcgggcg cgaccgacat ccgagcagcc | 5940 |
| gaggcttatg cgcccagcaa catcgcgctg tcgaaatact ggggcaagcg cgacgccgcg | 6000 |
| cggaaccttc cgctgaacag ctccgtctcg atctcgttgg cgaactgggg ctctcatacg | 6060 |
| cgggtcgagg ggtccggcac gggccacgac gaggtgcatc acaacggcac gctgctggat | 6120 |
| ccgggcgacg ccttcgcgcg ccgcgcgttg gcattcgctg acctgttccg ggggggggagg | 6180 |
| cacctgccgc tgcggatcac gacgcagaac tcgatcccga cggcggcggg gcttgcctcg | 6240 |
| tcggcctcgg ggttcgcggc gctgacccgt gcgctggcgg gggcgttcgg gctggatctg | 6300 |
| gacgacacgg atctgagccg catcgcccgg atcggcagtg gcagcgccgc ccgctcgatc | 6360 |
| tggcacggct tcgtccgctg gaaccggggc gaggccgagg atgggcatga cagccacggc | 6420 |
| gtcccgctgg acctgcgctg gccgggcttc cgcatcgcga tcgtggccgt ggacaagggg | 6480 |
| cccaagcctt tcagttcgcg cgacggcatg aaccacacgg tcgagaccag cccgctgttc | 6540 |
| ccgccctggc ctgcgcaggc ggaagcggat tgccgcgtca tcgaggatgc gatcgccgcc | 6600 |
| cgcgacatgg ccgccctggg tccgcgggtc gaggcgaacg cccttgcgat gcacgccacg | 6660 |
| atgatggccg cgcgcccgcc gctctgctac ctgacgggcg gcagctggca ggtgctggaa | 6720 |
| cgcctgtggc aggcccgcgc ggacgggctt gcggcctttg cgacgatgga tgccggcccg | 6780 |
| aacgtcaagc tgatcttcga ggaaagcagc gccgccgacg tgctgtacct gttccccgac | 6840 |
| gccagcctga tcgcgccgtt cgaggggcgt tgaacgcgta agacgaccac tgggtaaggt | 6900 |
| tctgccgcgc gtggtctcga ctgcctgcaa agaggtgctt gagttgctgc gtgactgcgg | 6960 |
| cggccgactt cgtgggactt gcccgccacg ctgacgaagg gcgaattcca gcacactggc | 7020 |
| ggccgttact agttctagag cggccgccac cgcggtggag gcggcacct cgctaacgga | 7080 |
| ttcaccgttt ttatca | 7096 |

<210> SEQ ID NO 3
<211> LENGTH: 1167
<212> TYPE: DNA
<213> ORGANISM: Paracoccus sp. R114

<400> SEQUENCE: 3

| | |
|---|---|
| atgaaagtgc ctaagatgac cgtgacagga atcgaagcga tcagcttcta caccccccag | 60 |
| aactacgtgg gactggatat ccttgccgcg catcacggga tcgaccccga gaagttctcg | 120 |
| aaggggatcg gcaggagaa atcgcactg cccggccatg acgaggatat cgtgaccatg | 180 |
| gccgccgagg ccgcgctgcc gatcatcgaa cgcgcgggca cgcagggcat cgacacggtt | 240 |
| ctgttcgcca ccgagagcgg gatcgaccag tcgaaggccg ccgccatcta tctgcgccgc | 300 |
| ctgctggacc tgtcgcccaa ctgccgttgc gtcgagctga agcaggcctg ctattccgcg | 360 |
| acggcggcgc tgcagatggc ctgcgcgcat gtcgcccgca agcccgaccg caaggtgctg | 420 |
| gtgatcgcgt ccgatgtcgc gcgctatgac cgcgaaagct cgggcgaggc gacgcagggt | 480 |
| gcgggcgccc tcgccatcct tgtcagcgcc gatcccaagg tggccgagat cggcaccgtc | 540 |
| tcggggctgt tcaccgagga tatcatggat ttctggcggc cgaaccaccg ccgcacgccc | 600 |
| ctgttcgacg gcaaggcatc gacgctcgcg tatctgaacg cgctggtcga ggcgtggaac | 660 |
| gactatcgcg cgaatggcgg ccacgagttc gccgatttcg cgcatttctg ctatcacgtg | 720 |
| ccgttctcgc ggatgggcga gaaggcgaac agccacctgg ccaaggcgaa caagacgccg | 780 |
| gtggacatgg ggcaggtgca gacgggcctg atctacaacc ggcaggtcgg gaactgctat | 840 |

```
accgggtcga tctacctggc attcgcctcg ctgctggaga acgctcagga ggacctgacc    900
ggcgcgctgg tcggtctgtt cagctatggc tcgggtgcga cgggcgaatt cttcgatgcg    960
cggatcgcgc ccggttaccg cgaccacctg ttcgcggaac gccatcgcga attgctgcag   1020
gatcgcacgc ccgtcacata tgacgaatac gttgccctgt gggacgagat cgacctgacg   1080
cagggcgcgc ccgacaaggc gcgcggtcgt ttcaggctgg caggtatcga ggacgagaag   1140
cgcatctatg tcgaccggca ggcctga                                       1167
```

<210> SEQ ID NO 4
<211> LENGTH: 388
<212> TYPE: PRT
<213> ORGANISM: Paracoccus sp. R114

<400> SEQUENCE: 4

```
Met Lys Val Pro Lys Met Thr Val Thr Gly Ile Glu Ala Ile Ser Phe
1               5                   10                  15

Tyr Thr Pro Gln Asn Tyr Val Gly Leu Asp Ile Leu Ala Ala His His
            20                  25                  30

Gly Ile Asp Pro Glu Lys Phe Ser Lys Gly Ile Gly Gln Glu Lys Ile
        35                  40                  45

Ala Leu Pro Gly His Asp Glu Asp Ile Val Thr Met Ala Ala Glu Ala
    50                  55                  60

Ala Leu Pro Ile Ile Glu Arg Ala Gly Thr Gln Gly Ile Asp Thr Val
65                  70                  75                  80

Leu Phe Ala Thr Glu Ser Gly Ile Asp Gln Ser Lys Ala Ala Ala Ile
                85                  90                  95

Tyr Leu Arg Arg Leu Leu Asp Leu Ser Pro Asn Cys Arg Cys Val Glu
            100                 105                 110

Leu Lys Gln Ala Cys Tyr Ser Ala Thr Ala Ala Leu Gln Met Ala Cys
        115                 120                 125

Ala His Val Ala Arg Lys Pro Asp Arg Lys Val Leu Val Ile Ala Ser
    130                 135                 140

Asp Val Ala Arg Tyr Asp Arg Glu Ser Ser Gly Glu Ala Thr Gln Gly
145                 150                 155                 160

Ala Gly Ala Val Ala Ile Leu Val Ser Ala Asp Pro Lys Val Ala Glu
                165                 170                 175

Ile Gly Thr Val Ser Gly Leu Phe Thr Glu Asp Ile Met Asp Phe Trp
            180                 185                 190

Arg Pro Asn His Arg Arg Thr Pro Leu Phe Asp Gly Lys Ala Ser Thr
        195                 200                 205

Leu Arg Tyr Leu Asn Ala Leu Val Glu Ala Trp Asn Asp Tyr Arg Ala
    210                 215                 220

Asn Gly Gly His Glu Phe Ala Asp Phe Ala His Phe Cys Tyr His Val
225                 230                 235                 240

Pro Phe Ser Arg Met Gly Glu Lys Ala Asn Ser His Leu Ala Lys Ala
                245                 250                 255

Asn Lys Thr Pro Val Asp Met Gly Gln Val Gln Thr Gly Leu Ile Tyr
            260                 265                 270

Asn Arg Gln Val Gly Asn Cys Tyr Thr Gly Ser Ile Tyr Leu Ala Phe
        275                 280                 285

Ala Ser Leu Leu Glu Asn Ala Gln Glu Asp Leu Thr Gly Ala Leu Val
    290                 295                 300

Gly Leu Phe Ser Tyr Gly Ser Gly Ala Thr Gly Glu Phe Phe Asp Ala
305                 310                 315                 320
```

Arg Ile Ala Pro Gly Tyr Arg Asp His Leu Phe Ala Glu Arg His Arg
                325                 330                 335

Glu Leu Leu Gln Asp Arg Thr Pro Val Thr Tyr Asp Glu Tyr Val Ala
            340                 345                 350

Leu Trp Asp Glu Ile Asp Leu Thr Gln Gly Ala Pro Asp Lys Ala Arg
        355                 360                 365

Gly Arg Phe Arg Leu Ala Gly Ile Glu Asp Glu Lys Arg Ile Tyr Val
    370                 375                 380

Asp Arg Gln Ala
385

<210> SEQ ID NO 5
<211> LENGTH: 1167
<212> TYPE: DNA
<213> ORGANISM: Paracoccus sp. R114

<400> SEQUENCE: 5
atgaaagtgc ctaagatgac cgtgacagga atcgaagcga tcagcttcta cacccccag      60 aactacgtgg gactggatat ccttgccgcg catcacggga tcgaccccga gaagttctcg    120
aaggggatcg gcaggagaa atcgcactg cccggccatg acgaggatat cgtgaccatg      180
gccgccgagg ccgcgctgcc gatcatcgaa cgcgcgggca cgcagggcat cgacacggtt    240
ctgttcgcca ccgagagcgg gatcgacaag tcgaaggccg ccgccatcta tctgcgccgc    300
ctgctggacc tgtcgcccaa ctgccgttgc gtcgagctga agcaggcctg ctattccgcg    360
acggcggcgc tgcagatggc ctgcgcgcat gtcgcccgca gcccgaccg caaggtgctg     420 gtgatcgcgt ccgatgtcgc gcgctatgac cgcgaaagct cgggcgaggc gacgcagggt    480
gcgggcgccg tcgccatcct tgtcagcgcc gatcccaagg tggccgagat cggcaccgtc    540
tcggggctgt tcaccgagga tatcatggat ttctggcggc cgaaccaccg ccgcacgccc    600
ctgttcgacg gcaaggcatc gacgctgcgc tatctgaacg cgctggtcga ggcgtggaac    660
gactatcgcg cgaatggcgg ccacgagttc gccgatttcg cgcatttctg ctatcacgtg    720
ccgttctcgc ggatgggcga gaaggcgaac agccacctgg ccaaggcgaa caagacgccc    780
gtggacatgg gcaggtgca gacgggcctg atctacaacc ggcaggtcgg aactgctat     840 accgggtcga tctacctggc attcgcctcg ctgctggaga cgctcagga ggaccctgacc   900 ggcgcgctgg tcggtctgtt cagctatggc tcgggtgcga cgggcgaatt cttcgatgcg    960
cggatcgcgc ccgttaccg cgaccacctg ttcgcggaac gccatcgcga attgctgcag   1020
gatcgcacgc ccgtcacata tgacgaatac gttgccctgt gggacgagat cgacctgacg   1080
cagggcgcgc ccgacaaggc gcgcggtcgt ttcaggctgg caggtatcga ggacgagaag   1140
cgcatctatg tcgaccggca ggcctga                                       1167

<210> SEQ ID NO 6
<211> LENGTH: 388
<212> TYPE: PRT
<213> ORGANISM: Paracoccus sp. R114

<400> SEQUENCE: 6

Met Lys Val Pro Lys Met Thr Val Thr Gly Ile Glu Ala Ile Ser Phe
1               5                   10                  15

Tyr Thr Pro Gln Asn Tyr Val Gly Leu Asp Ile Leu Ala Ala His His
            20                  25                  30

Gly Ile Asp Pro Glu Lys Phe Ser Lys Gly Ile Gly Gln Glu Lys Ile

-continued

```
                35                  40                  45
Ala Leu Pro Gly His Asp Glu Asp Ile Val Thr Met Ala Ala Glu Ala
 50                  55                  60

Ala Leu Pro Ile Ile Glu Arg Ala Gly Thr Gln Gly Ile Asp Thr Val
 65                  70                  75                  80

Leu Phe Ala Thr Glu Ser Gly Ile Asp Lys Ser Lys Ala Ala Ala Ile
                 85                  90                  95

Tyr Leu Arg Arg Leu Leu Asp Leu Ser Pro Asn Cys Arg Cys Val Glu
                100                 105                 110

Leu Lys Gln Ala Cys Tyr Ser Ala Thr Ala Leu Gln Met Ala Cys
                115                 120                 125

Ala His Val Ala Arg Lys Pro Asp Arg Lys Val Leu Val Ile Ala Ser
                130                 135                 140

Asp Val Ala Arg Tyr Asp Arg Glu Ser Ser Gly Glu Ala Thr Gln Gly
145                 150                 155                 160

Ala Gly Ala Val Ala Ile Leu Val Ser Ala Asp Pro Lys Val Ala Glu
                165                 170                 175

Ile Gly Thr Val Ser Gly Leu Phe Thr Glu Asp Ile Met Asp Phe Trp
                180                 185                 190

Arg Pro Asn His Arg Arg Thr Pro Leu Phe Asp Gly Lys Ala Ser Thr
                195                 200                 205

Leu Arg Tyr Leu Asn Ala Leu Val Glu Ala Trp Asn Asp Tyr Arg Ala
210                 215                 220

Asn Gly Gly His Glu Phe Ala Asp Phe Ala His Phe Cys Tyr His Val
225                 230                 235                 240

Pro Phe Ser Arg Met Gly Glu Lys Ala Asn Ser His Leu Ala Lys Ala
                245                 250                 255

Asn Lys Thr Pro Val Asp Met Gly Gln Val Gln Thr Gly Leu Ile Tyr
                260                 265                 270

Asn Arg Gln Val Gly Asn Cys Tyr Thr Gly Ser Ile Tyr Leu Ala Phe
                275                 280                 285

Ala Ser Leu Leu Glu Asn Ala Gln Glu Asp Leu Thr Gly Ala Leu Val
                290                 295                 300

Gly Leu Phe Ser Tyr Gly Ser Gly Ala Thr Gly Glu Phe Phe Asp Ala
305                 310                 315                 320

Arg Ile Ala Pro Gly Tyr Arg Asp His Leu Phe Ala Glu Arg His Arg
                325                 330                 335

Glu Leu Leu Gln Asp Arg Thr Pro Val Thr Tyr Asp Glu Tyr Val Ala
                340                 345                 350

Leu Trp Asp Glu Ile Asp Leu Thr Gln Gly Ala Pro Asp Lys Ala Arg
                355                 360                 365

Gly Arg Phe Arg Leu Ala Gly Ile Glu Asp Glu Lys Arg Ile Tyr Val
                370                 375                 380

Asp Arg Gln Ala
385

<210> SEQ ID NO 7
<211> LENGTH: 1002
<212> TYPE: DNA
<213> ORGANISM: Paracoccus zeaxanthinifaciens ATCC 21588

<400> SEQUENCE: 7
atgaacgtgc aggaagacgt ccgcaaacca ctggaccggc tggccgaggc gctggcaccc      60
gagatggagg ccgtgaacgc gctgatccgc gaacgcatgg ccagcaggca tgcgccgcgc     120
```

-continued

```
atccccgagg tgaccgccca cctgatcgag gccggcggca agcgcctgcg cccgatgctg      180
accctggccg cggcgaagct gcttggctat ggcggcccct atcacgtgca tctggccgcg      240
acggtcgaat tcatccacac cgcgaccctg ctgcatgacg acgtggtcga cgaaagccgc      300
cagcgccgcg ggcgtccgac ggcgaacctg ctgtgggaca caagtccag cgtgctggtc       360 ggcgattacc tgttcgcgcg cagcttccag ctgatggtcg aacccggcag catgcgcacg      420
ctcgagatcc tgtcgaacgc cgccgccacc atcgccgagg gcgaggtgct gcagctgacc      480
gcggcgcagg atctgccac gaacgaggac atctatctgc aggtcgtgcg cggcaagacg       540
gcagcgctgt tctcggccgc gaccgaggtg ggcggcgtca tcgcgggcgt ccccgatgcg      600
caggtccgcg cgctgttcga ttacggcgac gcgcttggca tcgccttcca gatcgtggac      660
gacctgctgg attacggcgg caccgccgag gcgatcggca agaataccgg cgacgatttc      720
cgcgaacgca agctgacgct gccggtgatc aaggccgtgg cccgcgccac ccccgaggaa      780
cgcgccttct ggtcgcgcac catcgagaag ggcgaccaga aggacggcga ccttgaacac      840
gcgctggaac tgctggcccg ccacggcgcg atggccgatg cccgccgcga cgcgctggac      900
tgggcggcca gggcccgcgc ctccctgcag atcctgcccg agcatccgat ccgcgacatg      960
ctgtcggacc tggccgattt cgtggtcgaa cgcatcgcct ga                        1002
```

<210> SEQ ID NO 8
<211> LENGTH: 333
<212> TYPE: PRT
<213> ORGANISM: Paracoccus zeaxanthinifaciens ATCC 21588

<400> SEQUENCE: 8

```
Met Asn Val Gln Glu Asp Val Arg Lys Pro Leu Asp Arg Leu Ala Glu
1               5                   10                  15

Ala Leu Ala Pro Glu Met Glu Ala Val Asn Ala Leu Ile Arg Glu Arg
            20                  25                  30

Met Ala Ser Arg His Ala Pro Arg Ile Pro Glu Val Thr Ala His Leu
        35                  40                  45

Ile Glu Ala Gly Gly Lys Arg Leu Arg Pro Met Leu Thr Leu Ala Ala
    50                  55                  60

Ala Lys Leu Leu Gly Tyr Gly Gly Pro Tyr His Val His Leu Ala Ala
65                  70                  75                  80

Thr Val Glu Phe Ile His Thr Ala Thr Leu Leu His Asp Asp Val Val
                85                  90                  95

Asp Glu Ser Arg Gln Arg Arg Gly Arg Pro Thr Ala Asn Leu Leu Trp
            100                 105                 110

Asp Asn Lys Ser Ser Val Leu Val Gly Asp Tyr Leu Phe Ala Arg Ser
        115                 120                 125

Phe Gln Leu Met Val Glu Pro Gly Ser Met Arg Thr Leu Glu Ile Leu
    130                 135                 140

Ser Asn Ala Ala Ala Thr Ile Ala Glu Gly Glu Val Leu Gln Leu Thr
145                 150                 155                 160

Ala Ala Gln Asp Leu Ala Thr Asn Glu Asp Ile Tyr Leu Gln Val Val
                165                 170                 175

Arg Gly Lys Thr Ala Ala Leu Phe Ser Ala Thr Glu Val Gly Gly
            180                 185                 190

Val Ile Ala Gly Val Pro Asp Ala Gln Val Arg Ala Leu Phe Asp Tyr
        195                 200                 205

Gly Asp Ala Leu Gly Ile Ala Phe Gln Ile Val Asp Asp Leu Leu Asp
```

-continued

```
            210                 215                 220
Tyr Gly Gly Thr Ala Glu Ala Ile Gly Lys Asn Thr Gly Asp Asp Phe
225                 230                 235                 240

Arg Glu Arg Lys Leu Thr Leu Pro Val Ile Lys Ala Val Ala Arg Ala
            245                 250                 255

Thr Pro Glu Glu Arg Ala Phe Trp Ser Arg Thr Ile Glu Lys Gly Asp
            260                 265                 270

Gln Lys Asp Gly Asp Leu Glu His Ala Leu Glu Leu Ala Arg His
        275                 280                 285

Gly Ala Met Ala Asp Ala Arg Arg Asp Ala Leu Asp Trp Ala Ala Arg
290                 295                 300

Ala Arg Ala Ser Leu Gln Ile Leu Pro Glu His Pro Ile Arg Asp Met
305                 310                 315                 320

Leu Ser Asp Leu Ala Asp Phe Val Val Glu Arg Ile Ala
                325                 330
```

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gcgctggtcg aggcgtggaa                                           20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cgtcagcgtg gcgggcaagt                                           20

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
aaggcctcat atgaacgtgc aggaagacgt                                30

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
cgggatcctc aggcgatgcg ttcgacca                                  28

<210> SEQ ID NO 13
<211> LENGTH: 31
<212> TYPE: DNA
<213> ORGANISM: Artificial Sequence
<220> FEATURE:
<223> OTHER INFORMATION: primer -continued

<400> SEQUENCE: 13
ggccgcgacg gtcgagttca tccacaccgc g                               31

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
cgcggtgtgg atgaactcga ccgtcgcggc c                               31

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
agagcgggat cgacaagtcg aaggccg                                    27

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
cggccttcga cttgtcgatc ccgctct                                    27

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
gtgcttgagt tgccgcgtga ctgcgg                                     26

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
ccgcagtcac gcggcaactc aagcac                                     26

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
cgtcaattat tacctccacg                                            20

<210> SEQ ID NO 20
<211> LENGTH: 20

```
<212> TYPE: DNA
<213> ORGANISM: Artificial Sequence
<220> FEATURE:
<223> OTHER INFORMATION: primer

<400> SEQUENCE: 20
ggccatgccc gtgacgcgat                                                    20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gagttcttct gagcgggact                                                    20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ccgacatagt tcttctcgta                                                    20

<210> SEQ ID NO 23
<211> LENGTH: 7096
<212> TYPE: DNA
<213> ORGANISM: Paracoccus sp. R114

<400> SEQUENCE: 23
cggctgggtg tggcggaccg ctatcaggac atagcgttgg ctacccgtga tattgctgaa          60
gagcttggcg gcgaatgggc tgaccgcttc ctcgtgcttt acggtatcgc cgctcccgat         120
tcgcagcgca tcgccttcta tcgccttctt gacgagttct tctgagcggg actctggggt         180
tcgaaatgac cgaccaagcg acgcccaacc tgccatcacg agatttcgat tccaccgccg         240
ccttctatga aggttgggc ttcggaatcg ttttccggga cgccggctgg atgatcctcc          300
agcgcgggga tctcatgctg gagttcttcg cccacccca tgggcaaata ttatacgcaa          360
ggcgacaagg tgctgatgcc gctggcgatt caggttcatc atgccgtttg tgatggcttc         420
catgtcggca gaatgcttaa tgaattacaa cagtttttat gcaacgcgtc gaaccgcccg         480
tccgacgccg gtttccgcac ggaaacgcgc ggcaagttga cataacttgc acgcgacgtc         540
tcgattctgc ccgcgaagaa tgcgatgcat ccagatgatg cagaacgaag aagcggaagc         600
gcccgtgaaa gaccagatga tttcccatac cccggtgccc acgcaatggg tcggcccgat         660
cctgttccgc ggccccgtcg tcgagggccc gatcagcgcg ccgctggcca cctacgagac         720
gccgctctgg ccctcgaccg cgcgggggc aggggtttcc cggcattcgg gcgggatcca          780
ggtctcgctg gtcgacgaac gcatgagccg ctcgatcgcg ctgcgggcgc atgacggggc         840
ggcggcgacc gccgcctggc agtcgatcaa ggcccgccag aagaggtcg cggccgtggt          900
cgccaccacc agccgcttcg cccgccttgt cgagctgaat cgccagatcg tgggcaacct         960
gctttacatc cgcatcgaat gcgtgacggg cgacgcctcg ggtcacaaca tggtcaccaa        1020
ggccgccgag gccgtgcagg gctggatcct gtcggaatac ccgatgctgg cctattccac        1080
gatctcgggg aacctgtgca ccgacaagaa ggcgtcggcg gtcaacgcca tcctgggccg        1140
```

-continued

```
cggcaaatac gccgtcgccg aggtcgagat cccgcgcaag atcctgaccc gcgtgctgcg    1200
caccagcgcc gagaagatgg tccgcctgaa ctacgagaag aactatgtcg ggggtacgct    1260
ggcggggtcg ctgcgcagtg cgaacgcgca tttcgccaac atgctgctgg gcttctacct    1320
ggcgacgggg caggacgcgg ccaacatcat cgaggccagc cagggcttcg tccattgcga    1380
ggcccgcggc gaggatctgt atttctcgtg cacgctgccc aacctcatca tgggctcggt    1440
cggtgccggc aagggcatcc cctcgatcga ggagaacctg tcgcggatgg gctgccgcca    1500
gccgggcgaa cccggcgaca acgcgcgccg tcttgcggcg atctgcgcgg gcgtcgtgct    1560
gtgtggtgaa ttgtcgctgc ttgcggccca gaccaacccc ggagagttgg tccgcaccca    1620
catggagatg gagcgatgac cgacagcaag gatcaccatg tcgcggggcg caagctggac    1680
catctgcgtg cattgacga cgatgcggat atcgaccggg gcgacagcgg cttcgaccgc    1740
atcgcgctga cccatcgcgc cctgcccgag gtggatttcg acgccatcga cacggcgacc    1800
agcttcctgg gccgtgaact gtccttcccg ctgctgatct cgtccatgac cggcggcacc    1860
ggcgaggaga tcgagcgcat caaccgcaac ctggccgctg gtgccgagga ggcccgcgtc    1920
gccatgcgcg tgggctcgca gcgcgtgatg ttcaccgacc cctcggcgcg ggccagcttc    1980
gacctgcgcg cccatgcgcc caccgtgccg ctgctggcca atatcggcgc ggtgcagctg    2040
aacatggggc tggggctgaa ggaatgcctg gccgcgatcg aggtgctgca ggcggacggc    2100
ctgtatctgc acctgaaccc cctgcaagag gccgtccagc ccgaggggga tcgcgacttt    2160
gccgatctgg gcagcaagat cgcggccatc gcccgcgacg ttcccgtgcc cgtcctgctg    2220
aaggaggtgg gctgcggcct gtcggcggcc gatatcgcca tcgggctgcg cgccgggatc    2280
cggcatttcg acgtggccgg tcgcggcggc acatcctgga gccggatcga gtatcgccgc    2340
cgccagcggg ccgatgacga cctgggcctg gtcttccagg actggggcct gcagaccgtg    2400
gacgccctgc gcgaggcgcg gcccgcgctt gcggcccatg atggaaccag cgtgctgatc    2460
gccagcggcg gcatccgcaa cggtgtcgac atggcgaaat gcgtcatcct ggggccgac    2520 atgtgcgggg tcgccgcgcc cctgctgaaa gcggcccaaa actcgcgcga ggcggttgta    2580
tccgccatcc ggaaactgca tctggagttc cggacagcca tgttcctcct gggttgcggc    2640
acgcttgccg acctgaagga caattcctcg cttatccgtc aatgaaagtg cctaagatga    2700
ccgtgacagg aatcgaagcg atcagcttct acaccccccca gaactacgtg ggactggata    2760
tccttgccgc gcatcacggg atcgaccccg agaagttctc gaaggggatc gggcaggaga    2820
aaatcgcact gcccggccat gacgaggata tcgtgaccat ggccgccgag gccgcgctgc    2880
cgatcatcga acgcgcgggc acgcagggca tcgacacggt tctgttcgcc accgagagcg    2940
ggatcgacaa gtcgaaggcc gccgccatct atctgcgccg cctgctggac ctgtcgccca    3000
actgccgttg cgtcgagctg aagcaggcct gctattccgc gacggcggcg ctgcagatgg    3060
cctgcgcgca tgtcgcccgc aagcccgacc gcaaggtgct ggtgatcgcg tccgatgtcg    3120
cgcgctatga ccgcgaaagc tcgggcgagg cgacgcaggg tgcgggcgcc gtcgccatcc    3180
ttgtcagcgc cgatcccaag gtggccgaga tcggcaccgt ctcggggctg ttcaccgagg    3240
atatcatgga tttctggcgg ccgaaccacc gccgcacgcc cctgttcgac ggcaaggcat    3300
cgacgctgcg ctatctgaac gcgctggtcg aggcgtggaa cgactatcgc gcgaatggcg    3360
gccacgagtt cgccgatttc gcgcatttct gctatcacgt gccgttctcg cggatgggcg    3420
agaaggcgaa cagccacctg gccaaggcga acaagacgcc ggtggacatg ggcaggtgc    3480 agacgggcct gatctacaac cggcaggtcg ggaactgcta taccgggtcg atctacctgg    3540
```

```
cattcgcctc gctgctggag aacgctcagg aggacctgac cggcgcgctg gtcggtctgt   3600
tcagctatgg ctcgggtgcg acgggcgaat tcttcgatgc gcggatcgcg cccggttacc   3660
gcgaccacct gttcgcggaa cgccatcgcg aattgctgca ggatcgcacg cccgtcacat   3720
atgacgaata cgttgccctg tgggacgaga tcgacctgac gcagggcgcg cccgacaagg   3780
cgcgcggtcg tttcaggctg gcaggtatcg aggacgagaa gcgcatctat gtcgaccggc   3840
aggcctgaag caggcgccca tgccccgggc aagctgatcc tgtccgggga acattccgtg   3900
ctctatggtg cgcccgcgct tgccatggcc atcgcccgct ataccgaggt gtggttcacg   3960
ccgcttggca ttggcgaggg gatacgcacg acattcgcca atctctcggg cggggcgacc   4020
tattcgctga agctgctgtc ggggttcaag tcgcggctgg accgccggtt cgagcagttc   4080
ctgaacggcg acctaaaggt gcacaaggtc ctgacccatc ccgacgatct ggcggtctat   4140
gcgctggcgt cgcttctgca cgacaagccg ccggggaccg ccgcgatgcc gggcatcggc   4200
gcgatgcacc acctgccgcg accgggtgag ctgggcagcc ggacggagct gcccatcggc   4260
gcgggcatgg ggtcgtctgc ggccatcgtc gcggccacca cggtcctgtt cgagacgctg   4320
ctggaccggc ccaagacgcc cgaacagcgc ttcgaccgcg tccgcttctg cgagcggttg   4380
aagcacggca aggccggtcc catcgacgcg gccagcgtcg tgcgcggcgg gcttgtccgc   4440
gtgggcggga acgggccggg ttcgatcagc agcttcgatt tgcccgagga tcacgacctt   4500
gtcgcgggac gcggctggta ctgggtactg cacgggcgcc ccgtcagcgg gaccggcgaa   4560
tgcgtcagcg cggtcgcggc ggcgcatggt cgcgatgcgg cgctgtggga cgccttcgca   4620
gtctgcaccc gcgcgttgga ggccgcgctg ctgtctgggg gcagccccga cgccgccatc   4680
accgagaacc agcgcctgct ggaacgcatc ggcgtcgtgc cggcagcgac gcaggccctc   4740
gtggcccaga tcgaggaggc gggtggcgcg gccaagatct gcggcgcagg ttccgtgcgg   4800
ggcgatcacg gcggggcggt cctcgtgcgg attgacgacg cgcaggcgat ggcttcggtc   4860
atggcgcgcc atcccgacct cgactgggcg cccctgcgca tgtcgcgcac ggggcggca   4920 cccgccccg cgccgcgtgc gcaaccgctg ccggggcagg gctgatggat caggtcatcc   4980
gcgccagcgc gccgggttcg gtcatgatca cgggcgaaca tgccgtggtc tatggacacc   5040
gcgccatcgt cgccgggatc gagcagcgcg cccatgtgac gatcgtcccg cgtgccgacc   5100
gcatgtttcg catcacctcg cagatcgggg cgccgcagca ggggtcgctg gacgatctgc   5160
ctgcgggcgg gacctatcgc ttcgtgctgg ccgccatcgc gcgacacgcg ccggacctgc   5220
cttgcgggtt cgacatggac atcacctcgg ggatcgatcc gaggctcggg cttggatcct   5280
cggcggcggt gacggtcgcc tgcctcggcg cgctgtcgcg gctggcgggg cggggaccg   5340 aggggctgca tgacgacgcg ctgcgcatcg tccgcgccat ccagggcagg ggcagcgggg   5400
ccgatctggc ggccagcctg catggcggct tcgtcgccta tcgcgcgccc gatgcggtg   5460 ccgcgcagat cgaggcgctt ccggtgccgc cggggccgtt cggcctgcgc tatgcgggct   5520
acaagacccc gacagccgag gtgctgcgcc ttgtggccga tcggatggcg ggcaacgagg   5580
ccgctttcga cgcgctctac tcccggatgg gcgcaagcgc agatgccgcg atccgcgcgg   5640
cgcaagggct ggactgggct gcattccacg acgcgctgaa cgaataccag cgcctgatgg   5700
agcagctggg cgtgtccgac gacacgctgg acgcgatcat ccgcgaggcg cgcgacgcgg   5760
gcgccgcagt cgccaagatc tccgctcgg ggctgggga ttgcgtgctg cactgggcg   5820 accagcccaa gggtttcgtg cccgcaagca ttgccgagaa gggacttgtt ttcgatgact   5880
```

-continued

```
gatgccgtcc gcgacatgat cgcccgtgcc atggcgggcg cgaccgacat ccgagcagcc    5940
gaggcttatg cgcccagcaa catcgcgctg tcgaaatact ggggcaagcg cgacgccgcg    6000
cggaaccttc cgctgaacag ctccgtctcg atctcgttgg cgaactgggg ctctcatacg    6060
cgggtcgagg ggtccggcac gggccacgac gaggtgcatc acaacggcac gctgctggat    6120
ccgggcgacg ccttcgcgcg ccgcgcgttg gcattcgctg acctgttccg ggggggagg    6180 cacctgccgc tgcggatcac gacgcagaac tcgatcccga cggcggcggg gcttgcctcg    6240
tcggcctcgg ggttcgcggc gctgacccgt gcgctggcgg gggcgttcgg gctggatctg    6300
gacgacacgg atctgagccg catcgcccgg atcggcagtg gcagcgccgc ccgctcgatc    6360
tggcacggct tcgtccgctg gaaccggggc gaggccgagg atgggcatga cagccacggc    6420
gtcccgctgg acctgcgctg gcccggcttc cgcatcgcga tcgtggccgt ggacaagggg    6480
cccaagcctt tcagttcgcg cgacggcatg aaccacacgg tcgagaccag cccgctgttc    6540
ccgccctggc ctgcgcaggc ggaagcggat tgccgcgtca tcgaggatgc gatcgccgcc    6600
cgcgacatgg ccgccctggg tccgcgggtc gaggcgaacg cccttgcgat gcacgccacg    6660
atgatggccg cgcgcccgcc gctctgctac ctgacgggcg gcagctggca ggtgctggaa    6720
cgcctgtggc aggcccgcgc ggacgggctt gcggcctttg cgacgatgga tgccggcccg    6780
aacgtcaagc tgatcttcga ggaaagcagc gccgccgacg tgctgtacct gttccccgac    6840
gccagcctga tcgcgccgtt cgaggggcgt tgaacgcgta agacgaccac tgggtaaggt    6900
tctgccgcgc gtggtctcga ctgcctgcaa agaggtgctt gagttgccgc gtgactgcgg    6960
cggccgactt cgtgggactt gcccgccacg ctgacgaagg gcgaattcca gcacactggc    7020
ggccgttact agttctagag cggccgccac cgcggtggag ggcggcacct cgctaacgga    7080
ttcaccgttt ttatca                                                   7096
```